(12) United States Patent
Cartledge et al.

(10) Patent No.: US 8,574,289 B2
(45) Date of Patent: Nov. 5, 2013

(54) INFLATABLE MINIMALLY INVASIVE SYSTEM FOR DELIVERING AND SECURING AN ANNULAR IMPLANT

(75) Inventors: Richard G. Cartledge, Boca Raton, FL (US); John P. Cartledge, Boca Raton, FL (US); James Badia, Redwood City, CA (US); James McCrea, Burlingame, CA (US); Luis Baez, Mountain View, CA (US); Peter Bentley, San Jose, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 303 days.

(21) Appl. No.: 12/702,502

(22) Filed: Feb. 9, 2010
(Under 37 CFR 1.47)

(65) Prior Publication Data
US 2011/0093062 A1    Apr. 21, 2011

Related U.S. Application Data

(60) Provisional application No. 61/151,061, filed on Feb. 9, 2009.

(51) Int. Cl.
*A61F 2/24*    (2006.01)
(52) U.S. Cl.
USPC ........ 623/2.11; 623/1.11; 623/1.12; 606/108; 604/96.01
(58) Field of Classification Search
None
See application file for complete search history.

(56) References Cited

U.S. PATENT DOCUMENTS

| | | | |
|---|---|---|---|
| 4,349,029 A * | 9/1982 | Mott | 604/103.07 |
| 4,445,892 A | 5/1984 | Hussein et al. | |
| 5,163,953 A | 11/1992 | Vince | |
| 5,492,532 A | 2/1996 | Ryan et al. | |
| 6,217,610 B1 * | 4/2001 | Carpentier et al. | 623/2.37 |
| 6,416,522 B1 * | 7/2002 | Strecker | 606/143 |
| 6,676,692 B2 * | 1/2004 | Rabkin et al. | 623/1.11 |
| 6,808,529 B2 | 10/2004 | Fulkerson | |
| 6,949,122 B2 * | 9/2005 | Adams et al. | 623/2.36 |
| 7,175,660 B2 | 2/2007 | Cartledge et al. | |
| 7,297,150 B2 | 11/2007 | Cartledge et al. | |
| 7,445,630 B2 | 11/2008 | Lashinski et al. | |
| 7,455,690 B2 | 11/2008 | Cartledge et al. | |
| 7,491,188 B2 * | 2/2009 | Holman et al. | 604/103.01 |

(Continued)

OTHER PUBLICATIONS

International Search Report dated Apr. 8, 2010.

(Continued)

*Primary Examiner* — Corrine M McDermott
*Assistant Examiner* — Todd J Scherbel
(74) *Attorney, Agent, or Firm* — Lerner, David, Littenberg, Krumholz & Mentlik, LLP

(57) ABSTRACT

A delivery device for an annular implant that includes a balloon expansion mechanism and an annular implant having an adjustable dimension. The balloon expansion mechanism includes an inflation tube attached to a non-occluding balloon collar which is supported by trusses radially extending from a trocar. The annular implant further includes a flexible ring core, contiguous coiled spacers, and anchoring blocks. The flexible ring core is adjusted via a cinching mechanism. The anchoring blocks are spaced along the ring core by the contiguous coiled spacers, which keeps the distance between each pair of anchoring blocks equidistant as the ring core diameter is manipulated by the device user. The annular implant can also include gunbarrel elements housed in the trocar. Each gunbarrel element contains a gunbarrel pusher which drives an attachment element into the annular implant and annular tissue.

10 Claims, 23 Drawing Sheets

(56) References Cited

U.S. PATENT DOCUMENTS

| | | | |
|---|---|---|---|
| 7,753,922 B2* | 7/2010 | Starksen | 606/144 |
| 7,914,576 B2* | 3/2011 | Navia et al. | 623/2.36 |
| 8,052,639 B2* | 11/2011 | Wilson | 604/103.07 |
| 2006/0074484 A1* | 4/2006 | Huber | 623/2.11 |
| 2006/0106405 A1 | 5/2006 | Fann et al. | |
| 2006/0241748 A1 | 10/2006 | Lee et al. | |
| 2006/0276887 A1* | 12/2006 | Brady et al. | 623/1.53 |
| 2007/0016287 A1 | 1/2007 | Cartledge et al. | |
| 2007/0219630 A1* | 9/2007 | Chu | 623/2.11 |
| 2007/0250161 A1* | 10/2007 | Dolan | 623/2.11 |
| 2007/0299543 A1 | 12/2007 | Cartledge et al. | |
| 2008/0027483 A1 | 1/2008 | Cartledge et al. | |
| 2008/0077235 A1* | 3/2008 | Kirson | 623/2.11 |
| 2008/0091213 A1 | 4/2008 | Jackson | |
| 2008/0109076 A1 | 5/2008 | Cartledge et al. | |
| 2008/0255506 A1* | 10/2008 | Wilson | 604/97.01 |
| 2008/0306586 A1* | 12/2008 | Cartledge et al. | 623/2.11 |
| 2009/0125102 A1 | 5/2009 | Cartledge et al. | |
| 2009/0234404 A1 | 9/2009 | Fitzgerald et al. | |
| 2010/0305609 A1 | 12/2010 | Cartledge et al. | |
| 2011/0009818 A1* | 1/2011 | Goff | 604/96.01 |
| 2011/0009956 A1 | 1/2011 | Cartledge et al. | |
| 2011/0022168 A1 | 1/2011 | Cartledge | |
| 2011/0066231 A1 | 3/2011 | Cartledge et al. | |
| 2011/0196480 A1 | 8/2011 | Cartledge | |
| 2011/0202130 A1 | 8/2011 | Cartledge et al. | |
| 2011/0208295 A1 | 8/2011 | Cartledge et al. | |
| 2011/0257633 A1 | 10/2011 | Cartledge et al. | |

OTHER PUBLICATIONS

U.S. Appl. No. 13/123,768.

Letter dated Jan. 27, 2011 from Richard H. Levinstein, Esq.

* cited by examiner

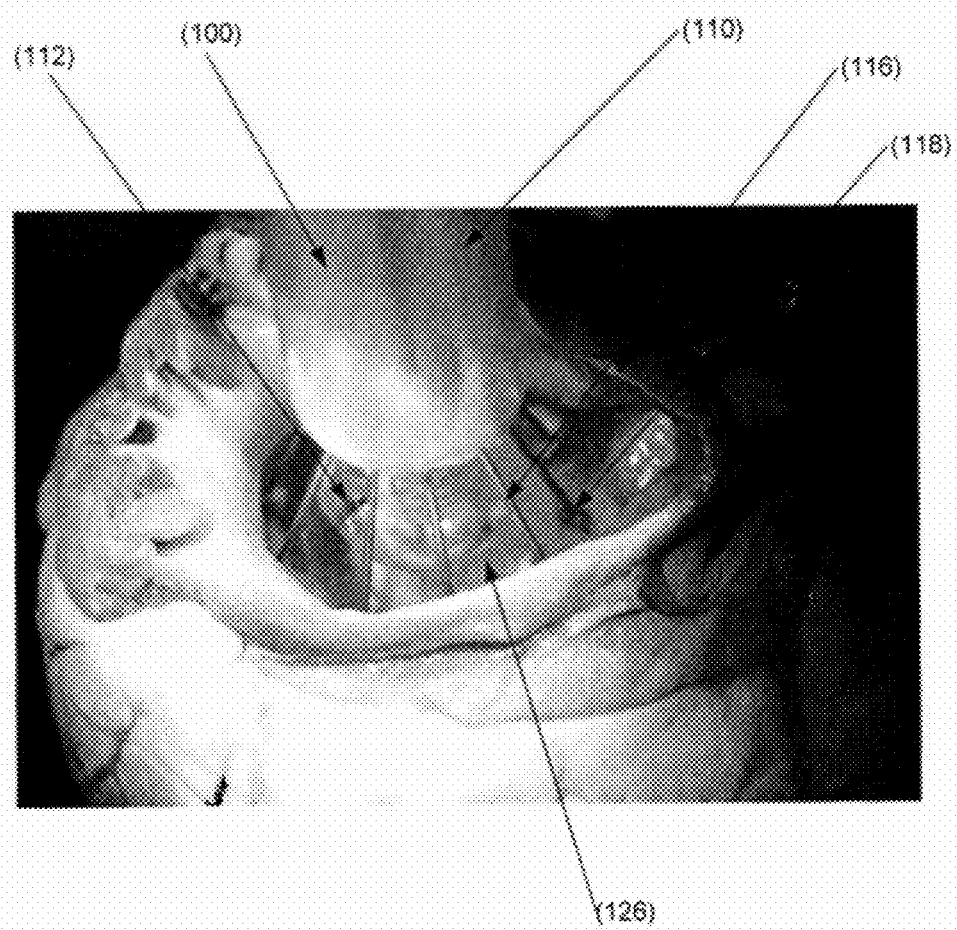

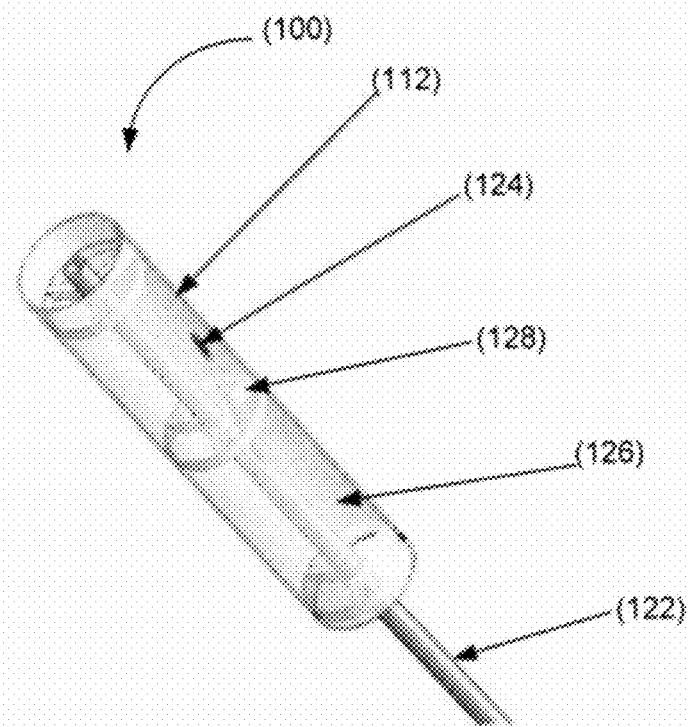

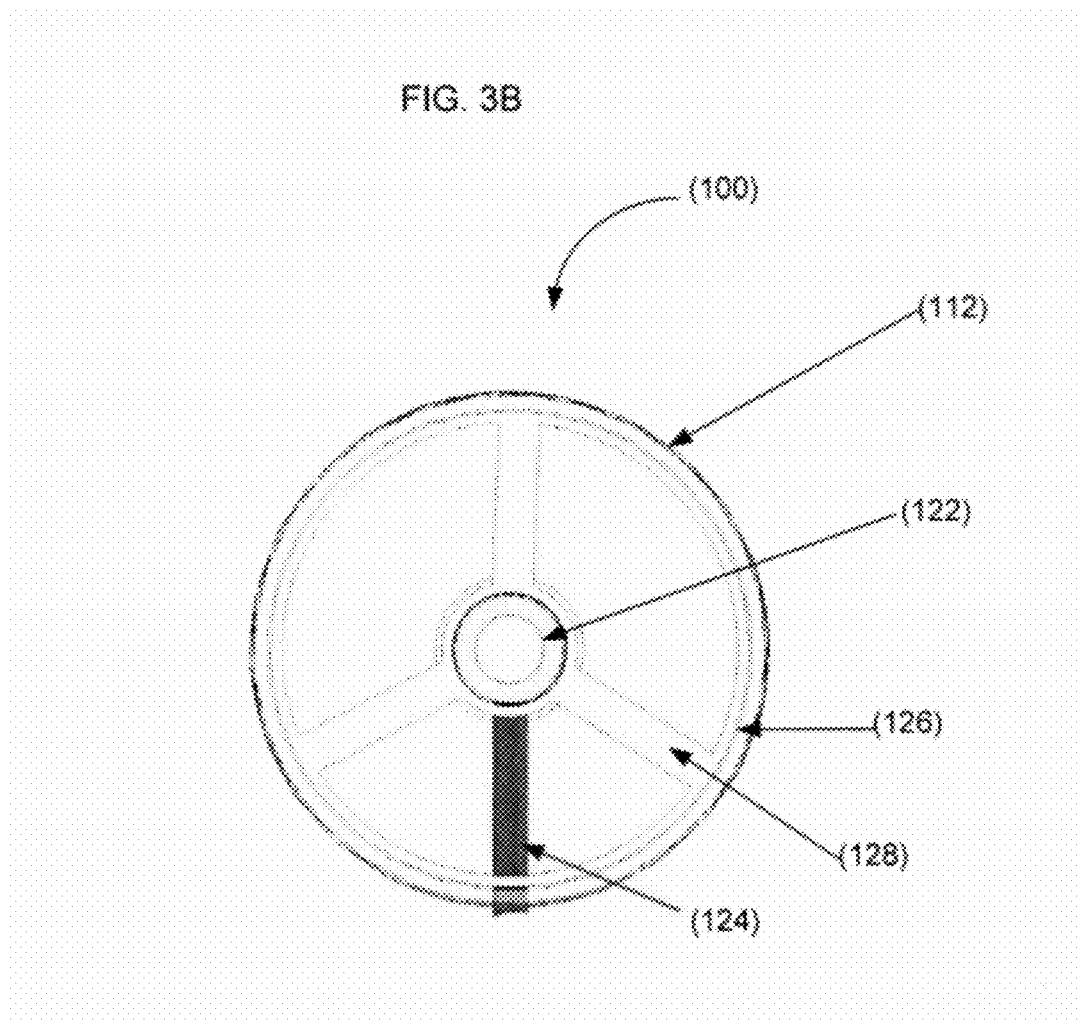

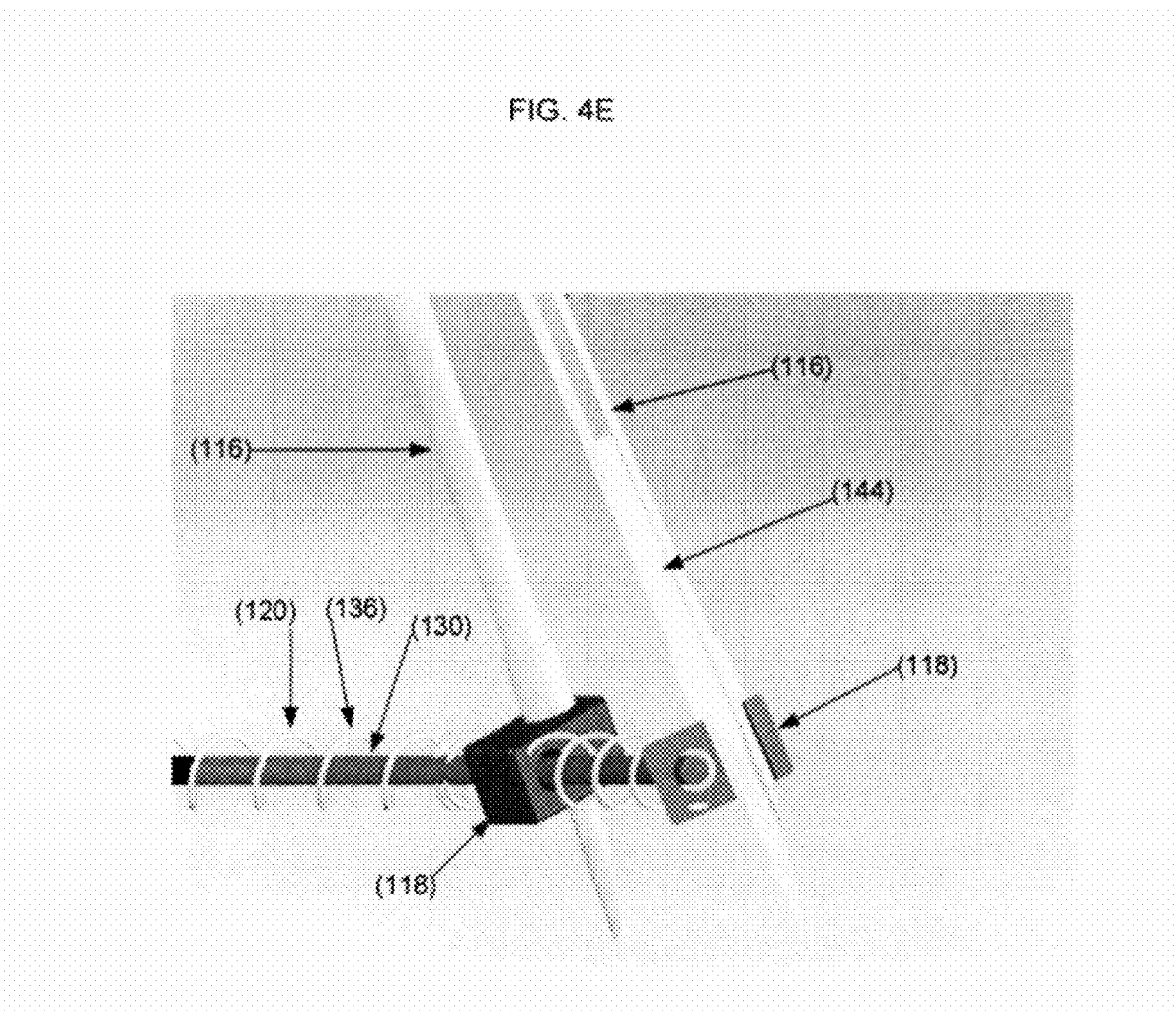

FIG. 5
FIG. 5A
FIG. 5B
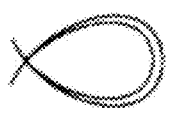
FIG. 5C
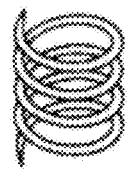
FIG. 5D
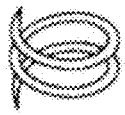
FIG. 5E
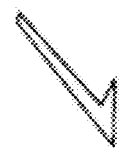
FIG. 5F
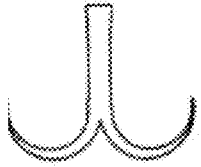
FIG. 5G
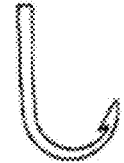
FIG. 5H

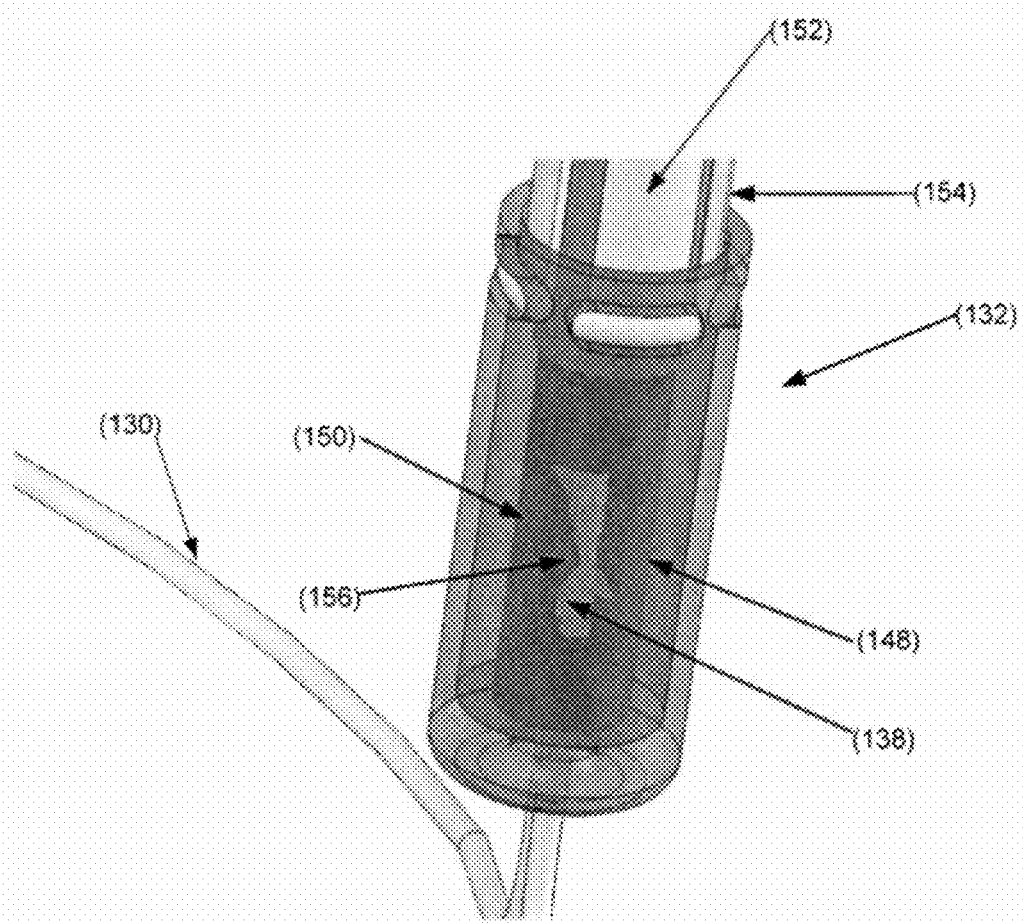

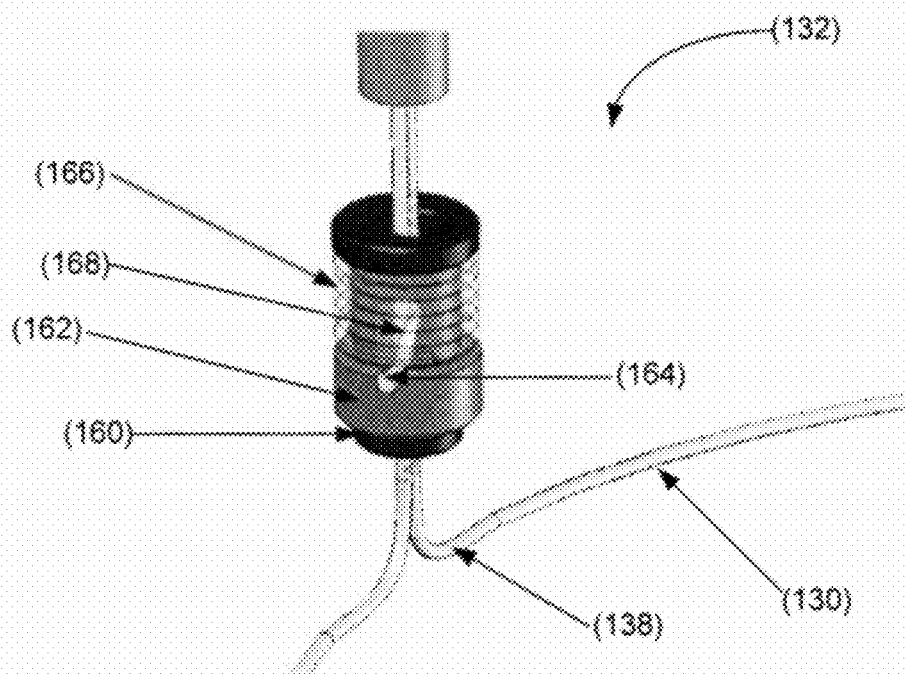

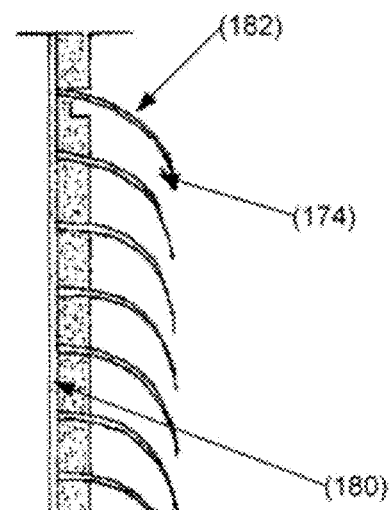
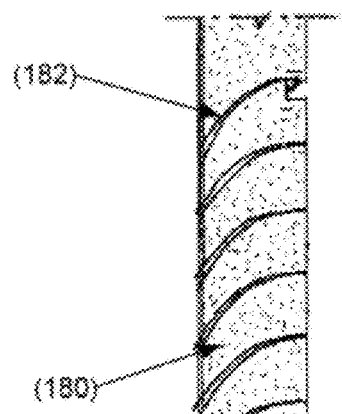
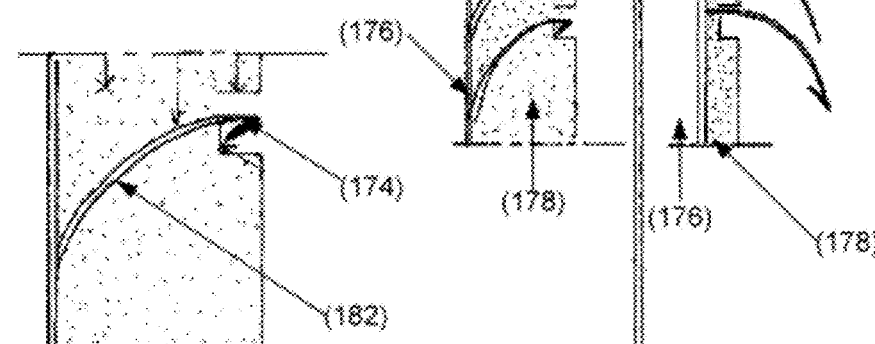

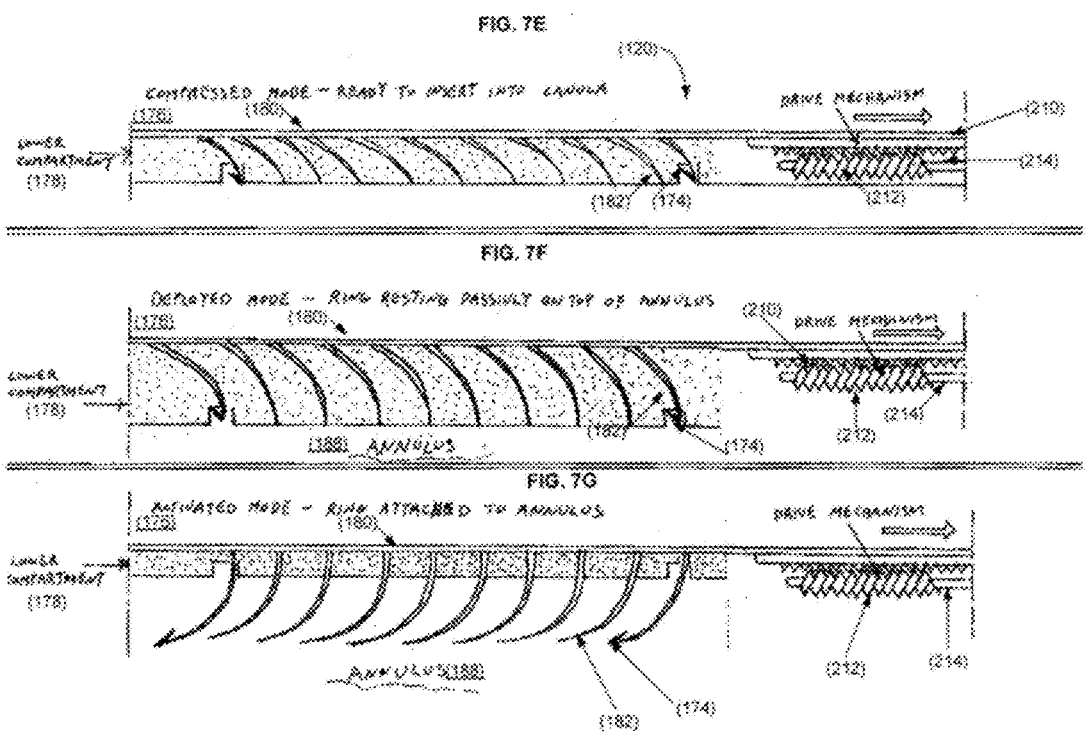

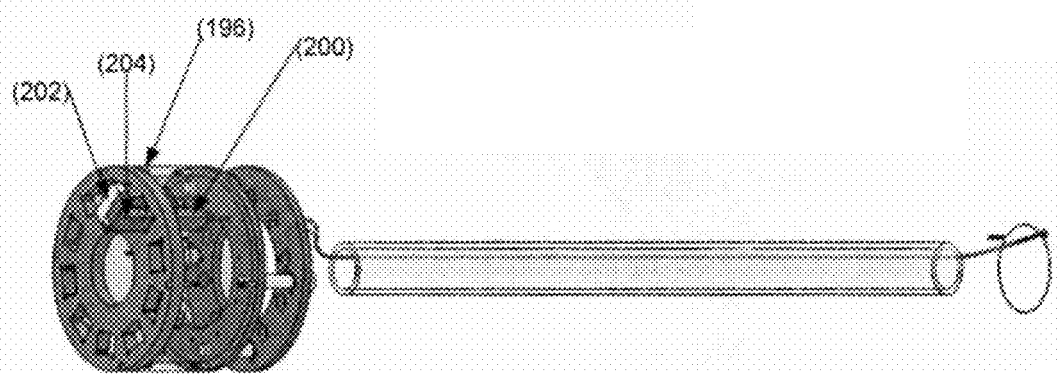
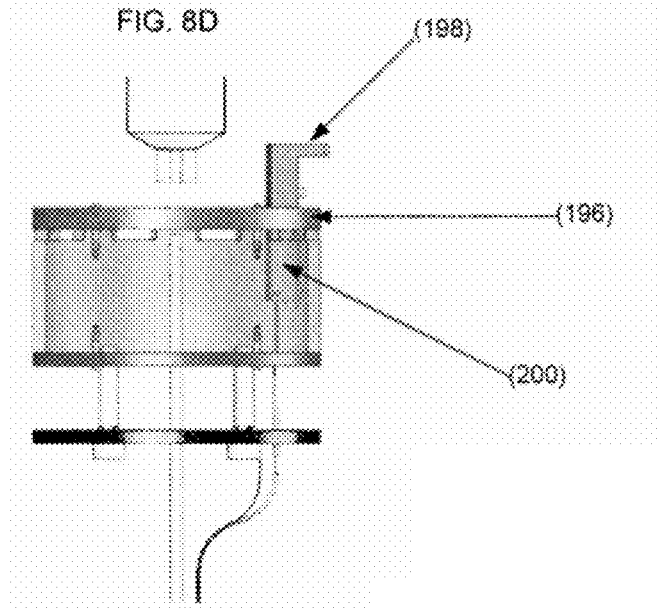

US 8,574,289 B2

INFLATABLE MINIMALLY INVASIVE SYSTEM FOR DELIVERING AND SECURING AN ANNULAR IMPLANT

CROSS REFERENCE TO RELATED APPLICATION

The application claims priority to U.S. Provisional Application No. 61/151,061, filed Feb. 9, 2009, which application is expressly incorporated herein by reference in its entirety.

FIELD OF THE INVENTION

The present invention relates generally to the delivery of an implantable device, and more particularly to methods and devices for delivering and securing an annular implant to control the internal circumference of an annulus.

BACKGROUND OF THE INVENTION

Many anatomic structures in the mammalian body are hollow passages in which walls of tissue define an annulus, which serves as a conduit for blood, other physiologic fluids, nutrient matter, or waste matter passing within the structure. In many physiologic settings, dysfunction may result from a structural annulus which is either too large or too small. In most such cases, dysfunction can be relieved by interventional changes in the size of the annulus.

Thus in surgery, there is often a need to reduce the internal circumference of an annulus or other open anatomic structure to narrow the size of the annulus or opening to achieve a desired physiologic effect. Often, such surgical procedures require interruption in the normal physiologic flow of blood, other physiologic fluids, or other structural contents through the annulus or structure. The exact amount of the narrowing required for the desired effect often cannot be fully appreciated until physiologic flow through the annulus or structure is resumed. It would be advantageous, therefore, to have an adjustable means of achieving this narrowing effect, such that the degree of narrowing could be changed not only after its implantation, but after the resumption of normal physiologic flow in situ.

One example of a dysfunction within an anatomic lumen is in the area of cardiac surgery, and specifically valvular repair. Approximately one million open heart surgical procedures are now performed annually in the United States, and twenty percent of these operations are related to cardiac valves.

The field of cardiac surgery was previously transformed by the introduction of the pump oxygenator, which allowed open heart surgery to be performed. Valvular heart surgery was made possible by the further introduction of the mechanical ball-valve prosthesis, and many modifications and different forms of prosthetic heart valves have since been developed. However, the ideal prosthetic valve has yet to be designed, which attests to the elegant form and function of the native heart valve. As a result of the difficulties in engineering a perfect prosthetic heart valve, there has been growing interest in repairing a patient's native valve. These efforts have documented equal long-term durability to the use of mechanical prostheses, with added benefits of better ventricular performance due to preservation of the subvalvular mechanism and obviation of the need for chronic anticoagulation. Mitral valve repair has become one of the most rapidly growing areas in adult cardiac surgery today.

Mitral valve disease can be subdivided into intrinsic valve disturbances and pathology extrinsic to the mitral valve ultimately affecting valvular function. Although these subdivisions exist, many of the repair techniques for and overall operative approaches to the various pathologies are similar.

Historically, most valvular pathology was secondary to rheumatic heart disease, a result of a streptococcal infection, most commonly affecting the mitral valve, followed by the aortic valve, and least often the pulmonic valve. The results of the infectious process are mitral stenosis and aortic stenosis, followed by mitral insufficiency and aortic insufficiency. With the advent of better antibiotic therapies, the incidence of rheumatic heart disease is on the decline, and accounts for a smaller percentage of valvular heart conditions in the developed world of the present day. Commissurotomy of rheumatic mitral stenosis was an early example of commonly practiced mitral valve repair outside of the realm of congenital heart defects. However, the repairs of rheumatic insufficient valves have not met with good results due to the underlying valve pathology and the progression of the disease.

Most mitral valve disease other than rheumatic results in valvular insufficiency that is generally amenable to repair. Chordae rupture is a common cause of mitral insufficiency, resulting in a focal area of regurgitation. Classically, one of the first successful and accepted surgical repairs was for ruptured chordae of the posterior mitral leaflet. The technical feasibility of this repair, its reproducible good results, and its long-term durability led the pioneer surgeons in the field of mitral valve repair to attempt repairs of other valve pathologies.

Mitral valve prolapse is a fairly common condition that leads over time to valvular insufficiency. In this disease, the plane of coaptation of the anterior and posterior leaflets is "atrialized" relative to a normal valve. This problem may readily be repaired by restoring the plane of coaptation into the ventricle.

The papillary muscles within the left ventricle support the mitral valve and aid in its function. Papillary muscle dysfunction, whether due to infraction or ischemia from coronary artery disease, often leads to mitral insufficiency (commonly referred to as ischemic mitral insufficiency). Within the scope of mitral valve disease, this is the most rapidly growing area for valve repair. Historically, only patients with severe mitral insufficiency had their mitral valve repaired or replaced, but there is increasing support in the surgical literature to support valve repair in patients with moderate insufficiency that is attributable to ischemic mitral insufficiency. Early aggressive valve repair in this patient population has been shown to increase survival and improve long-term ventricular function.

In addition, in patients with dilated cardiomyopathy the etiology of mitral insufficiency is the lack of coaptation of the valve leaflets from a dilated ventricle. The resultant regurgitation is due to lack of coaptation of the leaflets. There is a growing trend to repair these valves, thereby repairing the insufficiency and restoring ventricular geometry, and thus improving overall ventricular function.

The two essential features of mitral valve repair are to fix primary valvular pathology (if present) and to support the annulus or reduce the annular dimension using an implantable device that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using transesophageal echocardiography (TEE). If significant residual valvular insufficiency is then documented, the surgeon must re-arrest the heart, re-open the heart, and then repair or replace the valve. This increases overall operative, anesthesia, and bypass times, and therefore increases the overall operative risks.

If the implant used to reduce the annulus is larger than the ideal size, mitral insufficiency may persist. If the implant is too small, mitral stenosis may result. The need exists, therefore, for an adjustable implant that would allow a surgeon to adjust the annular dimension in situ in a beating heart under the guidance of TEE or another diagnostic modality to achieve optimal valvular sufficiency and function.

Cardiac surgery is but one example of a setting in which adjustment of the annular dimension of an anatomic orifice in situ would be desirable. Another example is in the field of gastrointestinal surgery, where the Nissen fundoplication procedure has long been used to narrow the gastro-esophageal junction for relief of gastric reflux into the esophagus. In this setting, a surgeon is conventionally faced with the tension between creating sufficient narrowing to achieve reflux control, and avoiding excessive narrowing that may interfere with the passage of nutrient contents from the esophagus into the stomach. "Gas bloat," which causes the inability to belch, is also a common complication of overnarrowing of the gastro-esophageal junction. Again, it would be desirable to have a method and apparatus by which the extent to which the gastro-esophageal junction is narrowed could be adjusted in situ to achieve optimal balance between those two competing interests.

Another example of a surgical procedure in need of improvement for narrowing an anatomic space is that for gastric bypass used in obesity control. In such a procedure, the goal is to reduce the available stomach volume adjacent to the esophagus in order to earlier stimulate satiation signaling with less food consumption. Prior art technologies include externally suturing or stapling a line of opposing stomach walls together to form a pouch in the upper stomach. This surgical strategy has the disadvantage of requiring invasive surgery to access the exterior of the stomach, and both sides thereof in the case of stapling with a required anvil, in addition to the lack of post operative adjustability of the pouch size. Alternative prior art gastric bypass attempts include encircling the stomach with an inflatable lap band, or Angel Chick prosthesis ring, to compress the stomach into smaller compartments. These techniques are disadvantageous again due to the surgically invasive procedure for applying the bands externally to the stomach, in addition to the high incidence of necrosis as the result of constricting the tissues.

Aside from the problem of adjusting the internal circumference of body passages in situ, there is often a need in medicine and surgery to place an implantable device at a desired recipient anatomic site. For example, existing methods proposed for percutaneous mitral repair include approaches through either the coronary sinus or percutaneous attempts to affix the anterior mitral leaflet to the posterior mitral leaflet. Significant clinical and logistical problems attend both of these existing technologies. In the case of the coronary sinus procedures, percutaneous access to the coronary sinus is technically difficult and time consuming to achieve, with procedures which may require several hours to properly access the coronary sinus. Moreover, many of these procedures employ incomplete annular rings, which compromise their physiologic effect. Moreover, the coronary sinus approach does not address the correction of diseased annular tissues, particularly on the posterior annulus of the mitral valve. Such procedures are typically not effective for improving mitral regurgitation by more than one clinical grade. Finally, coronary sinus procedures carry the potentially disastrous risks of either fatal tears or catastrophic thrombosis of the coronary sinus.

Similarly, percutaneous procedures which employ sutures, clips, or other devices to affix the anterior mitral leaflets to the posterior mitral leaflets also have limited reparative capabilities. Such procedures are also typically ineffective in providing a complete repair of mitral regurgitation. These procedures also fail to address the pathophysiology of the dilated mitral annulus in ischemic heart disease. As a result of the residual anatomic pathology, no annular repair, ventricular remodeling or improved ventricular function is likely with these procedures.

The need exists, therefore, for a delivery system and methods for its use that would avoid the need for open surgery in such exemplary circumstances, and allow delivery, placement, and adjustment of a prosthetic implant to reduce the diameter of a such an annulus in a percutaneous or other minimally invasive procedure, while still achieving clinical and physiologic results that are at least the equivalent of the yields of the best open surgical procedures for these same problems. Further, the need exists for a system that allows remote attachment of such an implant to the desired anatomic recipient site in a percutaneous or other minimally invasive procedure.

The need exists for implant delivery systems and methods which permit improved certainty of correct placement location thereof by visual and/or physical sensations of the operator. There exists a need for improved delivery systems which permit reshaping of the annular tissue to match the delivery configuration of the implant and insure consistent contact therewith for proper attachment. Furthermore, there exists a need to provide a minimally invasive delivery system for attaching an implant to adjacent tissues without manual placement of sutures or staples requiring opposing forces against the target tissues.

As mentioned, the preceding cardiac applications are only examples in which such a delivery system is desirable. Another exemplary application is in the field of gastrointestinal surgery, where the aforementioned Nissen fundoplication procedure has long been used to narrow the gastroesophageal junction for relief of gastric reflux into the esophagus. Gastric bypass surgery for treatment of moribund obesity is another field in need of improvement. There are many other potential applications in the broad fields of medicine and surgery. Among the other potential applications anticipated are adjustable implants for use in the treatment of urinary incontinence, anastomotic strictures, arterial stenosis, cervical incompetence, ductal strictures, and anal incontinence.

SUMMARY OF THE INVENTION

Devices and methods for delivering and securing an annular implant to control the internal circumference or shape of an annulus are provided by the present invention. The invention also provides devices and methods which permit improved certainty of preferred tissue placement location thereof by providing visual and/or physical information to the operator. The invention provides devices and methods which provide a minimally invasive delivery system for attaching an implant to adjacent tissues without sutures. These and many other advantages and features of the invention will become apparent to those skilled in the art upon reading the present specification of the preferred embodiments.

In one aspect, the device of the present invention provides a delivery device for an annular implant that includes a non-occluding inflatable balloon, a balloon expansion mechanism and an annular implant disposed thereon having an adjustable dimension. The balloon expansion mechanism includes an inflation tube attached to a non-occluding balloon collar which is supported by a plurality of trusses radially extending from a trocar. The annular implant has an adjustable dimension removably mounted around the non-occluding balloon collar. The non-occluding balloon collar is deliberately hollow, or tubular, so that blood may continue to flow through the annulus when the balloon is inflated.

The balloon collar can be inserted into the annulus in need of repair in its deflated position and then inflated. Alternatively, the balloon collar may be pre-inflated to its partially or fully expanded shape outside of the valve annulus, then advanced down through the annulus.

The annular implant may be positioned around the balloon collar so that its expansion and contraction is controlled by the expansion and contraction of the balloon. Alternatively, the annular implant may be independently introduced after the balloon collar is appropriately positioned in the annulus and delivered using the shape of the inflated balloon. Visual confirmation of the proper placement of the annular implant can be confirmed, such as with echocardiography or fluoroscopy, and radiopaque markings on the device.

In a preferred embodiment where the annulus includes an anatomical valve, such as a mitral valve, a mechanical check valve is incorporated into the delivery device. The check valve temporarily replaces the function of the biological valve, during the time that the balloon collar is distended and the biological valve is held open and non-functional. The check valve can be a monoleaflet, bileaflet, or ball/cage design, similar to mitral valve prosthetic devices known in the art.

In another preferred aspect, a device is provided for delivering and securing a flexible annular implant comprising a flexible ring core, contiguous coiled spacers, and anchoring blocks. The ring core and coiled spacers can be encased in a protective sheath. The anchoring blocks are spaced along the ring core by the contiguous coiled spacers, which keep a predetermined distance between each pair of anchoring blocks as the ring core diameter is manipulated by the device user. The anchoring blocks are attached to the ends of gunbarrel elements that extend from the tip of the delivery trocar during device operation. These gunbarrel elements house attachment elements for the implant, as described below, and can be pre-formed so as to flare radially outward as they extend from the tip of the trocar.

In a preferred embodiment, the ring core runs around the circumference of the device, then through a cinching mechanism. As the two ends of the ring core pass through the cinching mechanism, they become cinching cords, which pass up through the trocar of the device. The flared gunbarrel elements and the cinching cords allow the user to control the size of the ring core. The flared gunbarrel elements tend to expand the ring core diameter, whereas the cinching mechanism allows the user to reduce the ring core diameter or shape. The device user pulls on the exposed ends of the cinching cords located at the distal end of the trocar to reduce the diameter of the ring core. When the device user releases tension on the cinching cords, a locking mechanism prevents the ring core from relaxing and the ring diameter from consequently expanding, unless desired. Through a combination of extension of the gunbarrel elements from the trocar and tension exerted on the cinching cords, the device user can tailor the size and shape of the ring core. The locking mechanism may feature a means by which the user can release the lock, so that the ring may be readjusted as many times as necessary to achieve the desired result.

In certain embodiments, each gunbarrel element is secured into an anchoring block on the ring core. The gunbarrel elements are pre-shaped to expand the ring outwards, once the gunbarrel elements are pushed clear of the trocar. Each gunbarrel element contains a gunbarrel pusher and a hollow insert, both of which are activated by the device user via the control interface located outside of the patient's body. Once the device user determines that the ring core is positioned correctly upon the annulus, the device user activates each gunbarrel pusher, which drives an attachment element into the annular implant and the annular tissue.

After each attachment element has been deployed, the annular implant is securely attached to the annulus. A variety of modalities for assessing mitral function, such as real time trans esophageal echocardiography, intravascular echocardiography or fluoroscopy, and intracardiac echocardiography, may be used to assess the physiologic effect of the implant on the mitral function. Further adjustments of the device can alter the position, size and shape of the annular implant. Once a desired result has been achieved, the annular implant delivery device is retracted.

In another embodiment, a device is provided for anchoring and/or adjusting the annular implant. In this embodiment, a series of retention barbs may be integrally formed with or fixedly attached to the interior of the annular implant and are oriented to facilitate placement, retention, and removal of the annular implant.

The exemplary embodiment of this reversible attachment apparatus employs unidirectional retention barbs. The retention barbs are oriented in a consistent, tangential position with respect to the annular implant. The retention barbs may be further provided with a terminal hook, which allows for firm anchoring of the annular implant into the surrounding valve annulus. The retention barb/terminal hook apparatuses are movable between extended and retracted positions. A movable retainer guide located adjacent to the annular implant controls the action of the retention barbs, such as via a worm gear. In the retracted position, the retention barb/terminal hook apparatuses do not engage the valve annulus. When the movable retainer guide is engaged, the retention barb/terminal hook apparatuses extend through the annular implant and into the valve annulus. The terminal hooks act like anchors to fix the annular implant to the valve annulus.

Other systems, devices, methods, features and advantages of the disclosed delivery device for an annular implant will be apparent or will become apparent to one with skill in the art upon examination of the following figures and detailed description. All such additional systems, devices, methods, features and advantages are intended to be included within the description and are intended to be protected by the accompanying claims.

BRIEF DESCRIPTION OF THE DRAWINGS

The objects and advantages of the present invention will be better understood and more readily apparent when considered in conjunction with the following detailed description and accompanying drawings which illustrate, by way of example, a preferred embodiment and in which:

FIGS. 1A-C are a series of schematic views of the annular implant delivery device. FIG. 1A is a schematic view showing the insertion of the annular implant delivery device into and through the mitral annulus, with the gunbarrels deployed and the balloon collar deflated. FIG. 1B is a schematic view showing the insertion of the annular implant delivery device into and through the mitral annulus, with the gunbarrels deployed and the balloon collar expanded. FIGS. 1A-1B illustrate the delivery technique by which the balloon is positioned and expanded in the mitral annulus before the ring is delivered. FIG. 1C is a schematic view showing the ring positioned about a pre-inflated balloon and illustrates the delivery technique by which the ring and balloon are inserted simultaneously into the mitral annulus.

FIGS. 3A-E are a series of schematic views showing the non-occluding balloon element of the annular implant delivery device of FIG. 1. FIG. 3A is a three-dimensional view of the balloon expansion mechanism, with the balloon collar deflated. FIG. 3B is an end-on view of the balloon expansion mechanism, with the balloon collar deflated. FIG. 3C is a three-dimensional view of the balloon expansion mechanism, with the balloon collar inflated. FIG. 3D is a proximal-distal view of the balloon expansion mechanism. FIG. 3E is another proximal-distal view of the balloon expansion mechanism.

FIG. 4A shows the inside of the flexible annular implant. FIG. 4B shows the side view of the flexible annular implant. FIG. 4C shows the proximal-distal view of the flexible annular implant. FIG. 4D shows the close-up view of the gunbarrels and block assembly of the flexible annular implant. FIG. 4E shows a close-up view of a gun barrel and black assembly, whole and in cross-section.

FIG. 5A-H are perspective views of various embodiments of the attachment elements.

FIGS. 6A-E are a series of views showing various embodiments of the cinching mechanism depicted in 4A-C. FIG. 6A shows a beartrap cinch for locking the flexible ring core in place during adjustment. FIG. 6B shows a ratchet mechanism for locking the flexible ring core in place during adjustment. FIG. 6C shows a wedge-pin cinch for locking the flexible ring core in place during adjustment. FIG. 6D is a cross-section view of the wedge-pin cinch of FIG. 6C. FIG. 6E shows a simple cam system for locking the flexible ring core in place during adjustment.

FIGS. 7A-G are a series of views showing the reversible attachment apparatus element of the annular implant. FIG. 7A shows the side-view of the flexible annular implant containing the reversible attachment apparatus. FIG. 7B depicts one retention barb/terminal hook apparatus housed inside the lower compartment of the annular implant. FIG. 7C shows a side-view of the flexible annular implant containing the reversible attachment apparatus, whereby the retention barb/terminal hook apparatuses are in a retracted position. FIG. 7D shows a side-view of the flexible annular implant containing the reversible attachment apparatus, whereby the retention barb/terminal hook apparatuses are in an extended position. FIGS. 7E-G illustrate the variable modes of the reversible attachment apparatus of the annular implant. FIG. 7E depicts the compressed mode, whereby the device is in position to be inserted into the catheter. FIG. 7F depicts post-injection mode, whereby the annular implant rests passively on top of the valve annulus. FIG. 7G depicts the activated mode, whereby the annular implant is attached to the valve annulus via the retention barb/terminal hook apparatuses.

FIGS. 8A-D are a series of views showing the control interface of the annular implant delivery device. FIG. 8A is an over-head view of the control interface. FIG. 8B is a perspective view of the control interface. FIG. 8C is a perspective view of the control interface, trochar and annular implant. FIG. 8D is a side-view of the control interface.

DETAILED DESCRIPTION OF THE PREFERRED EMBODIMENTS

Figure 1B:
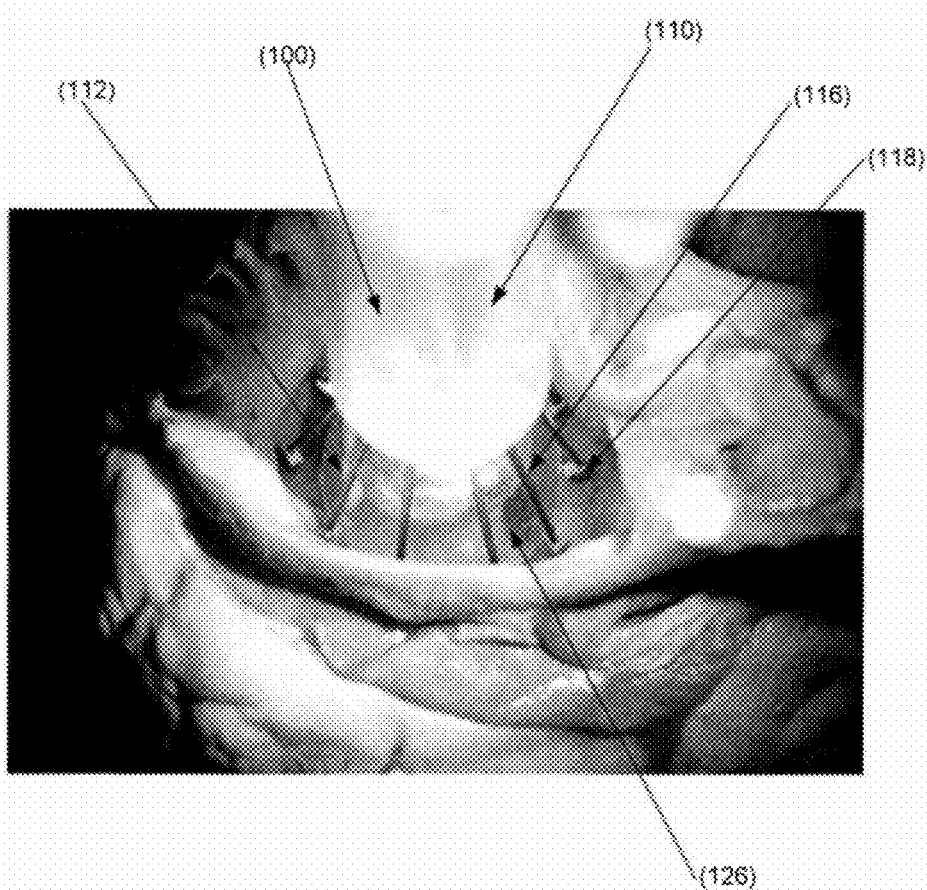

As required, detailed embodiments of the present invention are disclosed herein: however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

An improved annular implant delivery device has been developed for use in delivering an annular implant to an annulus in a patient's body. The delivery device can be housed in an endoscopic sheath or trocar or other covering, which is inserted into a patient to deliver an annular implant to an annulus in a minimally invasive procedure. The delivery procedure can be performed endoscopically, percutaneously, or with an endoscope placed within a body cavity or organ, or by trans-abdominal or trans-thoracic approaches. Thus, advantageously, the delivery device can help eliminate the need for an invasive surgical procedure. The delivery device can thereby help reduce the anesthesia and operative times required for a delivery procedure, as well as the risk associated with such a procedure, and the patient pain and recovery time following a procedure.

Devices and methods for delivering and securing an annular implant to control the internal circumference or shape of an annulus are provided by the present invention. The invention also provides devices and methods which permit improved certainty of tissue placement of the implant by providing visual and/or physical information to the operator. The invention provides devices and methods which remove unintended tissues from the site of implantation attachment during delivery. The invention provides devices and methods which permit reshaping of the annular tissue to match the delivery configuration of the implant and insure more consistent contact therewith for proper attachment to the implant. Furthermore, the invention provides devices and methods which provide a minimally invasive delivery system for attaching an implant to adjacent tissues without sutures requiring additional remote manual access or staples requiring opposing forces against the target tissues.

Therefore, the delivery device advantageously provides a means for pushing anatomical structures, such as mitral valves, out of the path of the device as it approaches the annulus, to help avoid damage to tissue around the annulus.

The device also advantageously provides a means of redesigning the size and shape of an annulus during implantation. The delivery device provides a structure for forcing the annulus to conform to the shape and size of the annular implant before securing the implant to the tissue, thereby creating a precise fit. The device further provides a structure for adjusting and maintaining the size and shape of the annulus as desired after the procedure to achieve a desired physiologic effect.

The delivery device also advantageously provides a means of incrementally adjusting the shape or circumference of the annular implant during a beating-heart or "off-pump" procedure, as well as after the procedure once the normal physiologic flow has resumed in situ. The delivery device thereby allows the shape or circumference of the annulus to be affected until the desired physiologic effect has been achieved. Further, the circumference or shape of the annular implant can be adjusted post-operatively, preferably percutaneously, to accommodate changes in the size, shape, or physiologic needs of the annulus.

In various embodiments, the delivery device may be employed to deliver an implant to internally adjustably constrict or expand the circumference or other dimensions of an annulus in which a disease process tends to enlarge such circumference or other dimensions. In additional various embodiments, the delivery device may be employed to deliver an implant to adjustably enlarge or maintain the circumference or other dimensions of an annulus in which a disease process tends to narrow or constrict such circumference or other dimensions. As used herein, "annulus" includes any substantially ring-like valve, sphincter, lumen, orifice, or other opening in the body. By way of illustration and not by way of limitation, recipient sites include a heart valve, blood vessels, the esophagus near the gastro-esophageal junction, the stomach, the anus, and the cervix.

In one aspect, the device of the present invention provides an annular implant having an adjustable dimension, such as the circumference of the annular implant. One embodiment of the delivery device of the present invention provides a balloon expansion mechanism whereby the annular implant is attached to a non-occluding balloon collar and delivered to the valve annulus via a catheter. The balloon expansion mechanism is similar to other balloon dilation catheters in the prior art, as disclosed in U.S. Pat. Nos. 6,872,223, 6,619,291, 6,217,610, and 6,168,614.

The balloon collar can be inserted in its deflated position and then inflated within the valve annulus to expand and deploy the annular implant, which can then be secured to the annulus with an attachment means or anchoring barbs. Alternatively, the balloon collar can be inserted in the valve annulus in a pre-determined inflated position. Once the balloon collar in its pre-determined inflated position is correctly positioned within the valve annulus, the annular implant can be deployed. Visual confirmation of the proper placement of the annular implant can be confirmed, such as with TEE.

In a preferred embodiment, the balloon expansion mechanism comprises a hollow catheter attached to an inflation tube whereby a gas or liquid is fed through said inflation tube and a non-occluding balloon collar is attached to the inflation tube to provide for expansion of the balloon collar. The balloon collar is supported by a plurality of wheel-shaped trusses extending from the catheter radially support the balloon collar. The balloon collar is deliberately hollow, or tubular, so that blood may continue to flow through the annulus when the balloon is inflated.

In a preferred embodiment, a check valve is incorporated into the balloon expansion mechanism. The check valve temporarily replaces the function of the mitral valve, during the time that the balloon collar is distended and the mitral valve open and non-functional. The check valve could be a monoleaflet, bileaflet, or ball/cage design, similar to mitral valve prosthetic devices known in the art.

Once the annular implant is properly positioned in the annulus, the balloon collar is deflated and removed. Such an operation may include elongating the balloon in the distal direction and reducing its radial dimension, for example, twisting. During the retraction of the balloon collar, care must be taken so as not to damage the valve leaflets.

The balloon expansion mechanism design offers some advantages over the "armed" annular expansion mechanisms. First, the balloon expansion mechanism can be operated with hydraulic pressure, which eliminates many of the geometrical versus load issues associated with the arm designs, in addition to making the design more amenable to a tortuous anatomy and percutaneous application. Second, the balloon has a generally soft surface as compared to the "armed" mechanisms, which should minimize trauma to the annulus when it is activated. Third, the balloon expansion mechanism pushes the entire annulus apart in one action, as opposed to the "armed" designs which may require a repeat of the expansion action followed by a rotation to find new anchoring points. Fourth, the distal end of the balloon design does not get entangled in any of the subvalvular apparatus.

In a preferred embodiment, a device is provided for delivering and securing a flexible annular implant composed of a flexible ring core, contiguous coiled spacers, and anchoring blocks. The anchoring blocks are spaced along the ring core by the contiguous coiled spacers, which keeps the distance between each pair of anchoring blocks equidistant as the ring core diameter is manipulated by the device user. The result of this design would be a ring that adjusts symmetrically about its entire circumference. The ring core runs around the circumference of the device, then through a cinching mechanism. As the two ends of the ring core pass through the cinching mechanism, they become cinching cords, which pass up through the trocar of the device. The device user pulls on the exposed ends of the cinching cords located at the distal end of the trocar to reduce the diameter of the ring core. When the device user releases tension on the cinching cords, a cinching mechanism (various embodiments detailed below and in FIGS. 6A-6E) prevents the ring core from relaxing and the ring diameter from consequently expanding, unless desired. Through a combination of extension of the gunbarrel elements from the trocar and tension exerted on the cinching cords, the device user can tailor the size of the ring core.

While the preferred embodiment results in a ring that adjusts symmetrically about its entire circumference, other embodiments are possible and could be used to selectively reduce certain segments of the ring more aggressively than others. For example, a ring could be designed with stiffer coiled spacers among the attachment blocks located on the anterior and posterior segments of the ring, with more compliant coiled spacers among the attachment blocks along the lateral sides of the ring. As this ring is cinched closed, the distance between the attachment blocks along the anterior and posterior segments would reduce more slowly than the distance between adjacent attachment blocks along the sides of the ring. The effect of this configuration would be a preferential septal/lateral adjustment to the ring during opening and closing.

Figure 8A:
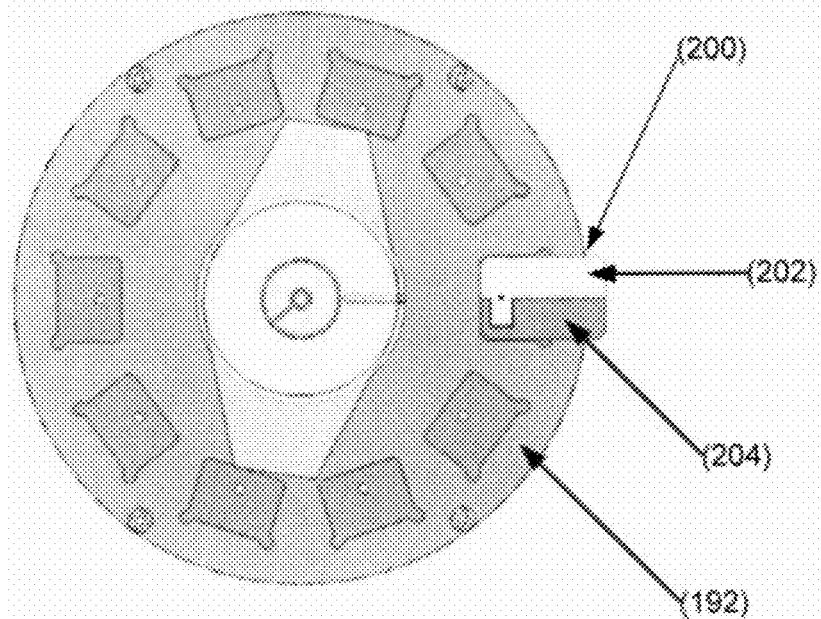
Figure 8B:
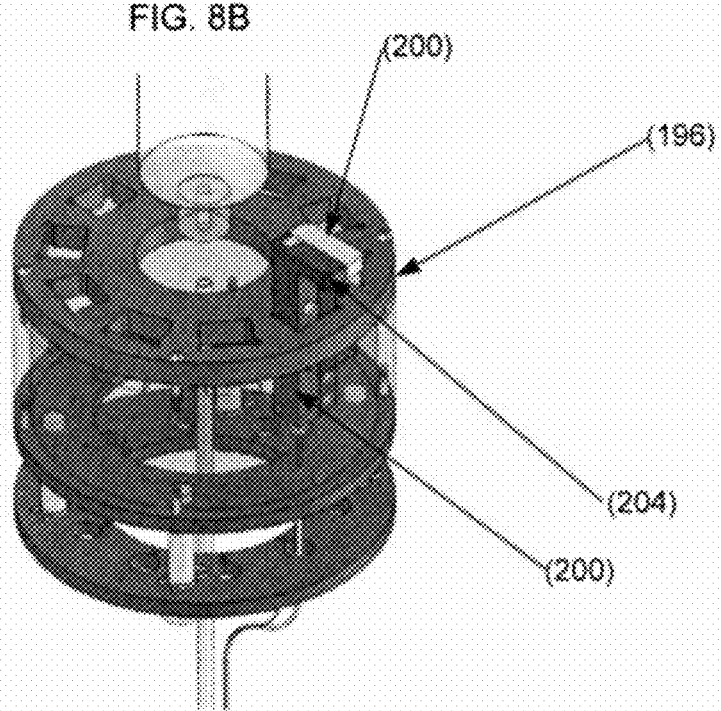

In certain embodiments, each gunbarrel element is secured into an anchoring block on the ring core. The gunbarrel elements are pre-shaped to expand the ring outwards, once the gunbarrel elements are pushed clear of the trocar. Each gunbarrel element contains a gunbarrel pusher and a hollow insert, both of which are activated by the device user via the control interface located outside of the patient's body (detailed below and in FIGS. 8A-B). Once the device user determines that the ring core is positioned correctly upon the valve annulus, the device user activates each gunbarrel pusher, which drives an attachment element into the annular implant and the annular tissue.

The gunbarrel elements, attachment elements or the annular implant may include touchdown sensors that detect contact with the annulus, to confirm that there is contact between the implant and the valve annulus at each point of attachment. The touchdown sensors can incorporate any mechanism known in the art, such as compressible buttons, resistance meters, or EKG sensors. In one embodiment, the touchdown sensors communicate with the control interface.

After each attachment element has been deployed, the annular implant is securely attached to the valve annulus. A variety of modalities for assessing mitral function, such as real time transesophageal echo echocardiography, intravascular echocardiography, and intracardiac echocardiography, may be used to assess the physiologic effect of the implant on the mitral function. Further adjustments of the device can alter the position, size and shape of the annular implant. Once a desired result has been achieved, the annular implant delivery device is retracted.

One embodiment of the cinching mechanism, which locks the ring core in place after adjustment, features a trap element which sits inside a hollow cylindrical housing. A pushrod sits atop the trap element. The cinching cords sit inside the trap element. At rest, the trap element is closed with the cinching cords jammed between the tapered feature located inside the trap element, thus allowing no adjustment of the ring core diameter. However, if a pushrod is engaged, the trap element is depressed, causing it to flex open. As the trap element flexes open, the tapered feature opens up, allowing the cinching cords to move freely. Releasing pressure on the pushrod causes the trap element to re-close, again cinching the cinching cords.

In various other embodiments of the cinching mechanism according to the present invention, the adjustment means may include a mechanism which may be threaded or non-threaded, and which may be engaged by the action of a screw or worm screw, a toothed mechanism, a ratchet mechanism, a rack and pinion mechanism, a wedge-pin mechanism, a cam-like structure or such other devices to permit discreet adjustment and retention of desired circumference of the ring core, once the proper size is determined.

In another embodiment, a device is provided for anchoring and/or adjusting the annular implant. In this embodiment, a series of retention barbs may be integrally formed with or fixedly attached to the interior of the annular implant and are oriented to facilitate placement, retention, and removal of the annular implant.

The exemplary embodiment of this reversible attachment apparatus employs unidirectional retention barbs. The retention barbs are oriented in a consistent, tangential position with respect to the annular implant. The retention barbs may be further provided with a terminal hook, which allows for firm anchoring of the annular implant into the surrounding valve annulus. The retention barb/terminal hook apparatuses are movable between extended and retracted positions. A movable retainer guide located adjacent to the annular implant controls the action of the retention barbs, such as via a worm gear. In the retracted position, the retention barb/terminal hook apparatuses do not engage the valve annulus. When the movable retainer guide is engaged, the retention barb/terminal hook apparatuses extend through the annular implant and into the valve annulus. The terminal hooks act like anchors to fix the annular implant to the valve annulus.

In another embodiment, a device is provided which acts as the main controller of each annular implant delivery device embodied in the present invention. The device, a control interface, is located outside of the patient's body and incorporates a plurality of attachment activator buttons, each of which drives a single attachment element into the annular implant and valve annulus by remotely controlling its movement.

The annular implant delivery device can be further understood with reference to the exemplary, non-limiting embodiments illustrated in FIGS. 1-8.

Figure 1C:
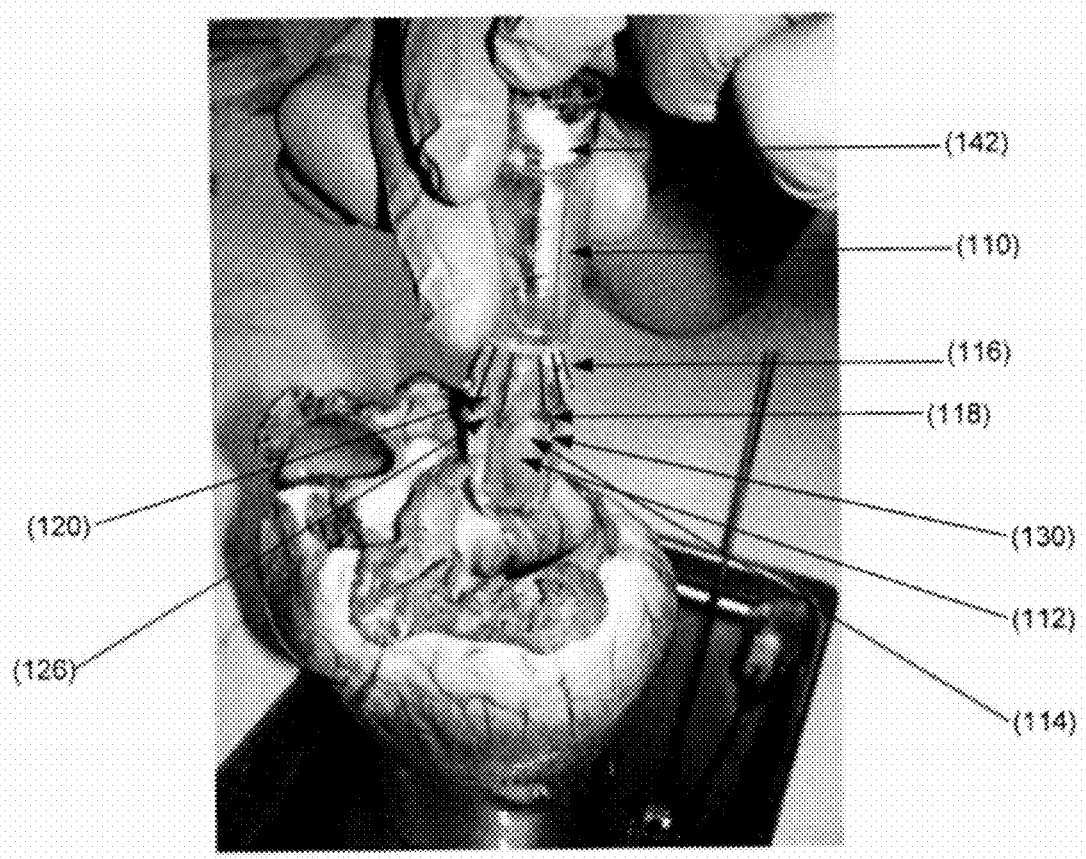

One embodiment of the annular implant delivery device is shown in FIG. 1A-C. The embodiment shown is designed for delivery of an annular implant to the mitral annulus of a heart.

In other embodiments, the delivery device is designed for any other annulus within the human body that is creating dysfunction that might be relieved by an implant capable of changing the size and shape of that site and maintaining a desired size and shape after surgery.

Figure 2:
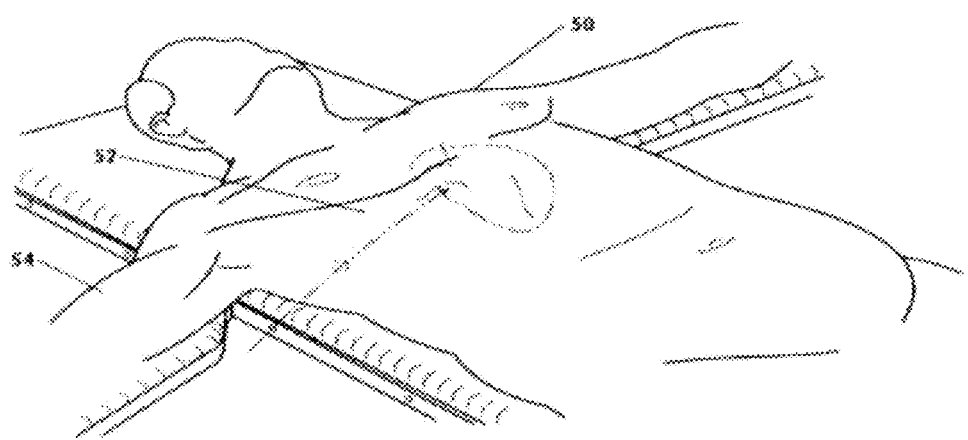
FIG. 2 is a schematic view of a patient in the supine position preparing for implantation of an annular device.

FIG. 2 shows a patient 50 in supine position preparing to undergo a minimally invasive procedure for mitral valve repair provided by one embodiment of the device of the present invention. The right lateral aspect of the patient's chest 52 is exposed by raising the right arm 54. The patient 50 has been sedated, anesthetized and intubated for surgery. The right lung has been deflated. An initial incision between the ribs is made for insertion of an endoscopic camera for viewing of the pericardium. Additional incisions are made for insertion of forceps and scissors for the removal of a portion of the pericardium. A purse string stitch is made in the left atrial wall, and an incision is made into the atrial wall of the heart while tensioning the purse string with a Ramel. The annular implant delivery device (not shown), is then advanced through the atrial wall incision while sufficiently loosening and then re-tightening the Ramel.

The annular implant delivery device 100 shown in FIGS. 1A-C includes a trocar 110, a balloon expansion mechanism 112, a balloon collar 126, gunbarrel elements 116, and anchoring blocks 118, as well as an annular implant 120. The number of gunbarrel elements 116 and anchoring blocks 118 can vary. For simplicity, the delivery device 100 is shown to include ten gunbarrel elements 116 anchored into ten anchoring blocks 118. In preferred embodiments, the device includes 2 to 12 or more gunbarrel elements 116 positioned in a circular shape. The gunbarrel elements 116 may be configured to other similar shapes such as oval, kidney bean or saddle-shaped, depending on the desired shape of the recipient annulus. The gunbarrel elements 116 may be a metallic, plastic, synthetic, or any other biologically-compatible material, or combination thereof. In one embodiment, the gunbarrel elements 116 are made of titanium.

The more proximal portion of the gunbarrel elements 116 are housed in the trocar 110. The alignment disc 142 located on the interior of the trocar 110 provides separation to the gunbarrel elements 116 so that they do not become twisted and entangled during the device introduction. Each gunbarrel element 116 contains a gunbarrel pusher (not shown) and a hollow insert (not shown), both of which are activated by the device user via the control interface located outside of the patient's body (detailed below and in FIGS. 8A-B). The control interface provides a means of remotely controlling the movement of each hollow insert and gunbarrel pusher, which drives the attachment element into the annular tissue.

The portion of the gunbarrel elements 116 adjacent to the annular implant 120 can be constructed of or labeled with an echo-opaque and/or a radio-opaque material for visualization of the alignment against the implant and tissues. Alternatively, aspects of the gunbarrel elements 116 can be constructed of thicker or thinner material to contrast with the portions of the gunbarrel elements adjacent to the annular implant 120. Such distinguishing marking enables a surgeon to visualize the location of the gunbarrel elements 116 and correspondingly, the annular implant 120, with respect to the recipient site during the delivery procedure using TEE or other imaging modalities.

The shape and size of the annular implant 120 should be chosen according to the anatomic needs of the intended recipient site. Like the gunbarrel elements 116, the implant 120 may be round or have other similar shapes such as oval, kidney bean or saddle-shaped, depending on the desired shape of the recipient annulus. Use of the terms "circumference" and "radius" and modifications thereof does not denote that the referenced structure, in most cases, the implant 120, is circular. For non-circular shapes, such as a kidney bean, "circumference" is used to mean the distance around the perimeter of the shape. Particularly useful implants include those described in U.S. Pat. No. 7,297,150 and U.S. Ser. No. 11/802,264 which are hereby incorporated by reference in their entirety.

The composition of the annular implant 120 should also be chosen according to the needs of the recipient site. The implant 120 can be accordion-like or it may have a smooth surface. In various embodiments, the annular implant 120 may be a solid structure, a tubular or otherwise hollow structure, or a structure with an outer member and an inner member. In the latter embodiment, the outer member of the implant body may serve as a covering for the implant 120, and may be designed to facilitate and promote tissue ingrowth and biologic integration to the annulus. The outer member in such an embodiment may be fabricated of a biologically compatible material, such as Dacron, PUT, malleable metals, other biologically compatible materials, or a combination of such biologically compatible materials in a molded, woven, or non-woven configuration. The outer member in such an embodiment also serves to house the inner member. Further, at least some portions of the adjustable inner or outer member may be elastic to provide an element of variable, artificial muscle tone to a valve, sphincter, orifice or lumen in settings where such variability would be functionally valuable, such as in the treatment of rectal incontinence or vaginal prolapse.

During delivery of the annular implant, the annular implant is secured to the delivery device. In one embodiment, the annular implant is attached to a balloon collar and delivered to the valve annulus via the balloon expansion mechanism (shown in detail FIGS. 3A-E). The annular implant can be formed from a deformable material, and the balloon collar inflated within the valve annulus to expand and deploy the annular implant. In embodiments such as those described in FIGS. 3A-E, it will be appreciated that the balloon collar may be progressively expanded via the balloon expansion mechanism.

As shown in FIGS. 3A-E, the balloon expansion mechanism 112 of the annular implant delivery device 100 provides for the inflation of the balloon collar 126 with either liquid or gas. The balloon expansion mechanism 112 is composed of a hollow catheter 122 which feeds gas or liquid (such as saline) into the inflation tube 124 to provide for expansion of the balloon collar 126. The balloon collar 126 is deliberately hollow, or tubular, so that blood may continue to flow through the annulus when the balloon 114 is inflated. A plurality of wheel-shaped trusses 128 extending from the catheter 122 radially support the balloon 114.

In one embodiment (FIGS. 3D-E), a check valve 216 is incorporated into the balloon expansion mechanism 112. The check valve 216 would temporarily replace the functionality of an anatomical valve, such as the mitral valve, during the time that the balloon 114 is distended and the valve leaflets have been left open and non-functional. The check valve 216 could be a monoleaflet, bileaflet, or ball/cage design, similar to mitral valve prosthetic devices known in the art.

Figure 3C:
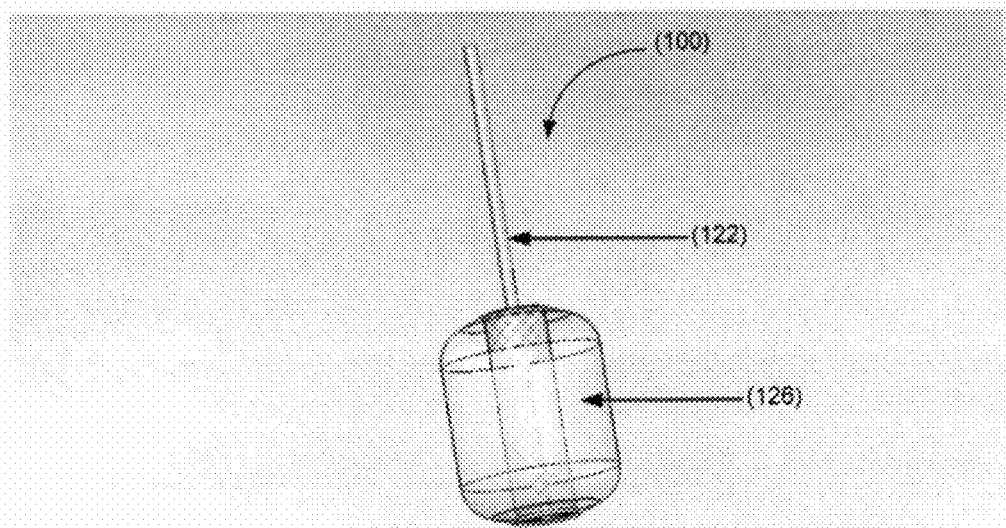
Figure 3D:
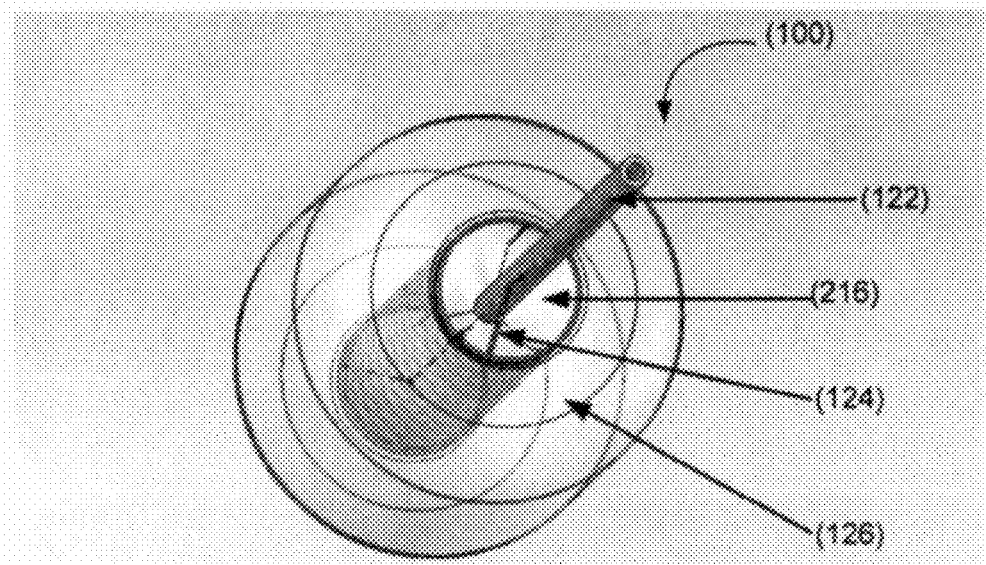
Figure 3E:
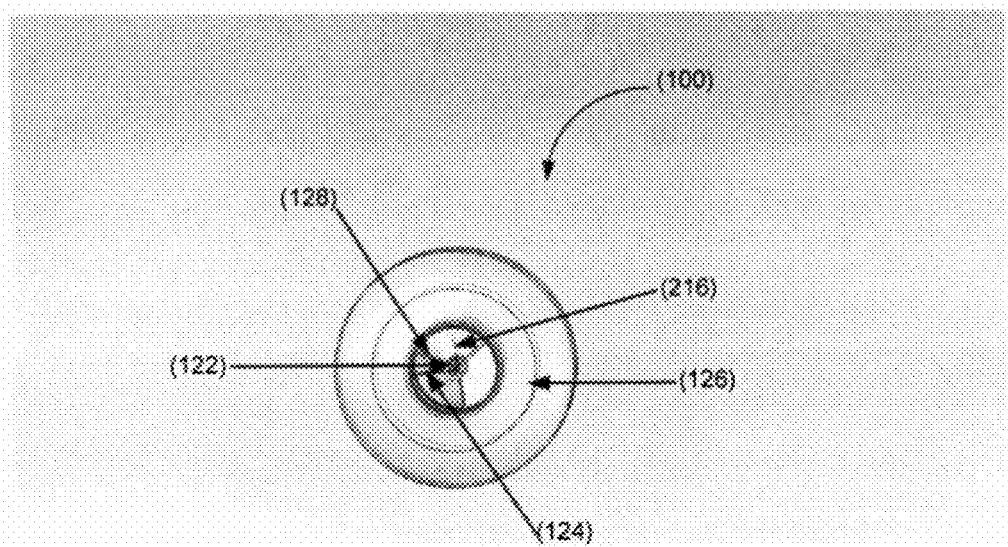

As the balloon collar 126 inflates with gas or liquid (as shown in FIG. 3C), it presses upon the mitral valve leaflets. The leaflets are pushed away until they are flush against the side of the heart. At this point, the outer surface of the balloon collar 126 is pushing against the mitral annulus. The annular implant 120 located around the balloon collar 126 is then secured to the annulus, such as with the attachment means or anchoring barbs as described below. Visual confirmation of the proper placement of the annular implant 120 can be confirmed, such as with TEE.

In a preferred embodiment, the balloon collar 126 is cylindrical or substantially cylindrical in shape. In other embodiments, the balloon collar 126 may be of any size and shape suitable for deployment in a lumen. The balloon 114 is preferably made of a flexible biocompatible material. In one embodiment, the balloon 114 is elastomeric, ranging from very soft to very rigid stiffness. In a preferred embodiment, the balloon 114 is made from an elastomeric material of medium stiffness. In another embodiment, the balloon 114 has a predefined inflated shape and pressure. Materials for the construction of balloons of the present invention preferably include polyurethane, polyethylene terephthalate (PET), polyethylene, polypropylene, polyesters and fluoropolymers.

FIGS. 4A-E depict a series of schematic views showing the flexible annular implant 120 with gunbarrel elements 116. The ring core 130 of the annular implant 120 is a flexible material made of wire, braided wire or suture material. The ring core 130 runs around the circumference of the device, then through a cinching mechanism 132. As the ring core 130 passes through the cinching mechanism 132, it becomes individual cords, hereafter referred to as the cinching cords 138, which pass up through the trocar 110.

The device user pulls on the exposed ends of the cinching cords 138 located at the distal end of the trocar 110 to control the diameter of the ring core 130. Pulling on the cinching cords 138 reduces the size of the ring core 130. When the device user releases tension on the cinching cords 138, a cinching mechanism 132 (various embodiments detailed below) prevents the ring core 130 from relaxing and the ring diameter from consequently growing. Through a combination of extension of the gunbarrel elements 116 from the trocar 110 (described below) and tension exerted on the cinching cords 138, the device user can tailor the size of the ring core 130.

The ring core 130 is held in a circular shape by the gunbarrel elements 116, which are pre-shaped to expand the ring outwards, once the gunbarrel elements 116 are pushed clear through of the trocar 110. The alignment disc 142 located on the interior of the trocar 110 provides separation to the gunbarrel elements 116 so that they do not become twisted and entangled during the device introduction. Each gunbarrel element 116 contains a gunbarrel pusher (not shown) and a hollow insert (not shown), both of which are activated by the device user via the control interface located outside of the patient's body (detailed below and in FIGS. 8A-B). The gunbarrel pusher drives the attachment element 144 into the annular implant and the annular tissue.

Each gunbarrel element 116 is secured into an anchoring block 118 on the ring core 130. Each anchoring block 118 anchors its respective gunbarrel element 116 to a particular position on the ring core 130. The anchoring blocks 118 are spaced by the contiguous coiled spacers 136, which keeps the distance between each pair of anchoring blocks 118 equidistant, or at any pre-selected distance, as the ring core 130 diameter is manipulated by the device user.

Each anchoring block 118 contains an opening through which the ring core 130 passes, which secures the anchoring blocks 118 to the ring core 130, thereby becoming a part of the annular implant 120. When the ring core 130 is positioned correctly upon the valve annulus, the device user deploys the buttons on the control interface to attach the annular implant 120 to the valve (detailed below and in FIGS. 4A-B). Particularly useful gunbarrel and pusher configurations can be seen in U.S. patent Ser. No. 12/026,624 which is hereby incorporated by reference. Once deployed, the attachment elements 144 penetrate the body of the anchoring blocks 118, thereby securing the anchoring blocks 118 to the valve annulus. The hollow inserts 140 of the gunbarrel elements 116 are angled outward in order to prohibit the attachment elements 144 from connecting into the valve leaflets or interfering with the balloon expansion mechanism 112.

The surgeon may also confirm the position of the gunbarrel elements 116 before advancing the attachment elements through the valve annulus. The region of each gunbarrel element 116 distal to the annular implant 120 can be labeled with an echo-opaque or radio-opaque material, allowing the surgeon to view the location of the gunbarrel elements 116 and annular implant 120 using TEE or other imaging modalities.

Attachment elements 144 can have a multiplicity of forms. The attachment elements 144 may be a metallic, plastic, synthetic, or any other biologically-compatible material, or combination thereof. In one embodiment, the attachment element 144 is made of a shape memory alloy. In a preferred embodiment, the shape memory alloy is nitinol. The configuration of the attachment element 144 can also vary. Examples of various embodiments of the attachment element 144 are shown in FIGS. 5A-H. The attachment element 144 in its relaxed position can be in the shape of a curve, as shown in FIG. 5A; a loop, as shown in FIG. 5B; a coil, as shown in FIG. 5C; a multi-coiled spiral, as shown in FIG. 5D; a two-coiled spiral, as shown in FIG. 5E; a rod with a barb, as shown in FIG. 5F; a bifurcated rod, as shown in FIG. 5G; or an anchor, as shown in FIG. 5H. The attachment element 144 can also be a pin or screw.

The gunbarrel elements, attachment elements or the annular implant 120 may include touchdown sensors that detect contact with the annulus, to confirm that there is contact between the implant and the valve annulus at each point of attachment. The touchdown sensors can incorporate any mechanism known in the art, such as compressible buttons, resistance meters, or EKG sensors. In one embodiment, the touchdown sensors communicate with the control interface.

Figure 4A:
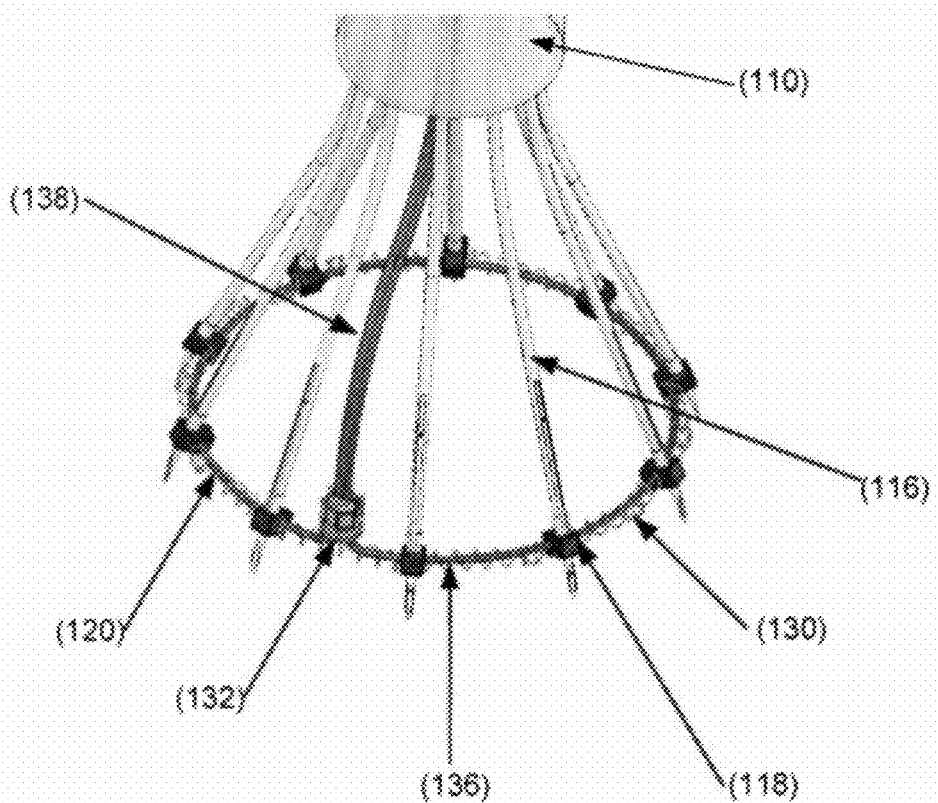
FIGS. 4A-D are a series of schematic views showing the flexible annular implant composed of a flexible ring core, contiguous coiled spacers, and anchoring blocks, appropriately positioned by gunbarrel elements.
Figure 4B:
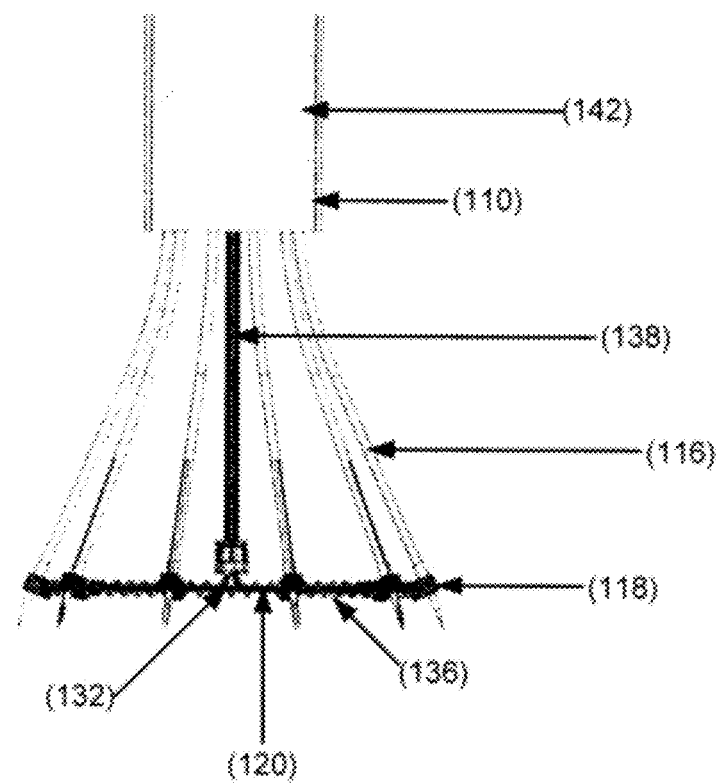
Figure 4C:
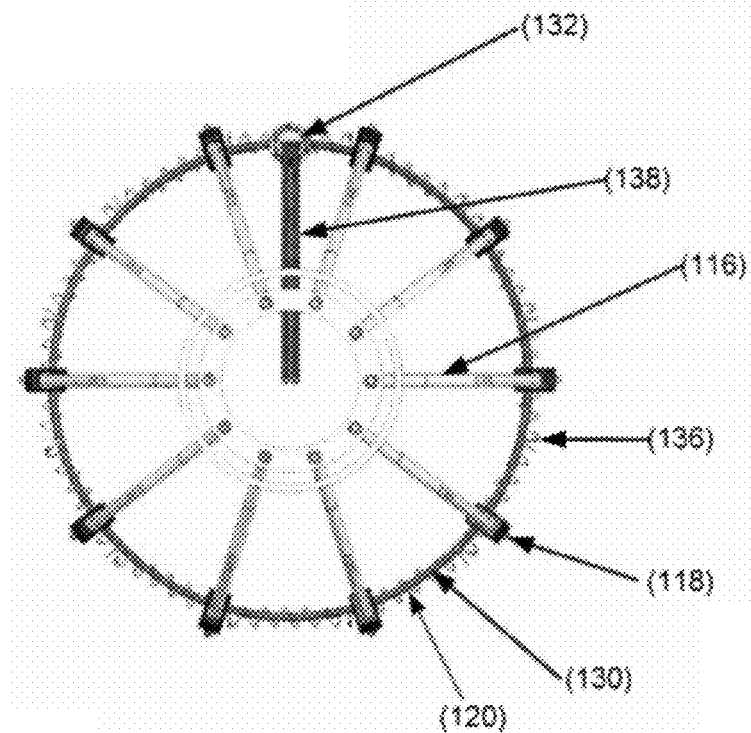
Figure 4D:
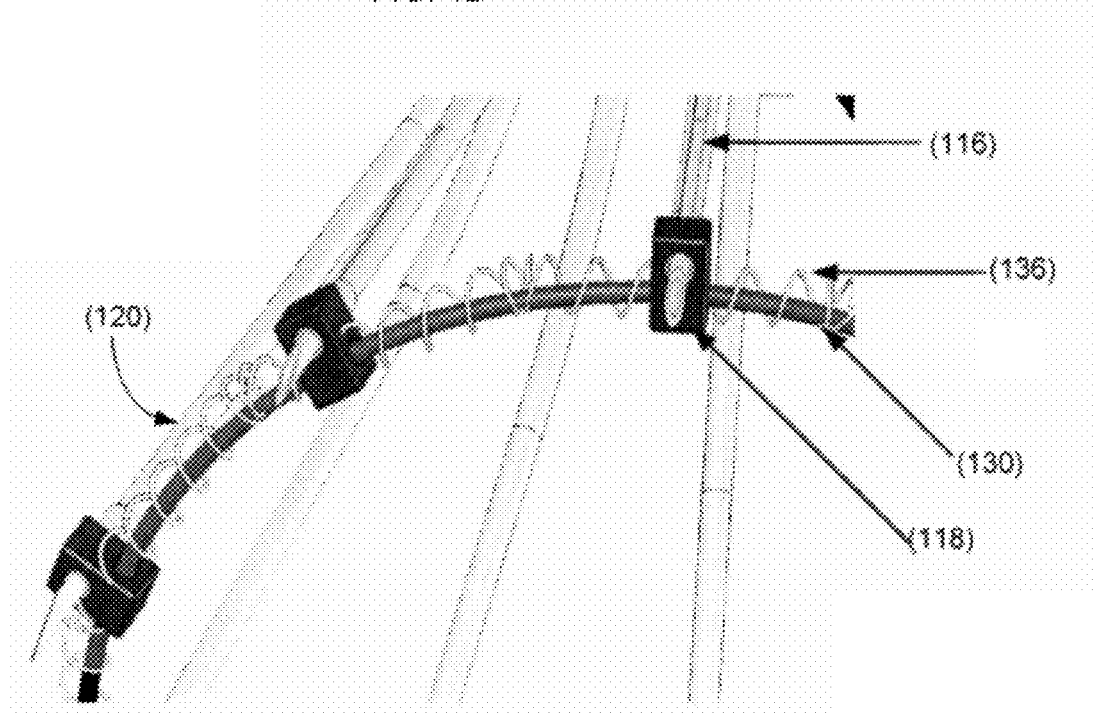

FIGS. 6A-E are a series of views showing various embodiments of the cinching mechanism 132 (depicted in FIGS. 4A-C). The cinching mechanism 132 locks the ring core 130 in place after adjustment. The various embodiments of the cinching mechanism 132 (detailed below) are controlled at the control interface 196 via a system of rods and wires, as appropriate. Controls consist of wires to pull the ring core 130 material together, a control to engage/release a lock for the cinching mechanism 132, and a tool (not shown) that cuts the excess cinching wire at a point proximal to the locking mechanism, allowing excess wire at a point proximal to the locking mechanism, allowing excess wire to be removed.

One embodiment of the cinching mechanism 132 (shown in FIG. 6A) features a trap element 148 which sits inside a hollow cylindrical housing 150. A pushrod 152 sits atop the trap element 148. An attachment tube 154 surrounds the pushrod 152. The cinching cords 138 sit inside the trap element 148. At rest, the trap element 148 is closed with the cinching cords 138 jammed between the tapered feature 156 located inside the trap element 148. However, if a pushrod 152 is engaged, the trap element 148 is depressed, causing it to flex open. As the trap element 148 flexes open, the tapered feature 156 opens up, allowing the cinching cords 138 to move freely, thereby allowing for adjustment of the flexible ring core (130). Releasing pressure on the pushrod 152 causes the trap element 148 to re-close, again cinching the cinching cords 138, thereby causing the diameter of the flexible ring core to lock. After the ring size is positioned at its prescribed dimension, the pushrod 152 is pulled upward causing the tines 158 located on the attachment tube 154 to flex inward, allowing the pushrod-attachment tube assembly 152, 154 to pull free. The trap element 148 and hollow cylindrical housing 150 remain attached to the cinching cords 138 in order to keep the ring core 130 locked in place.

Figure 6B:
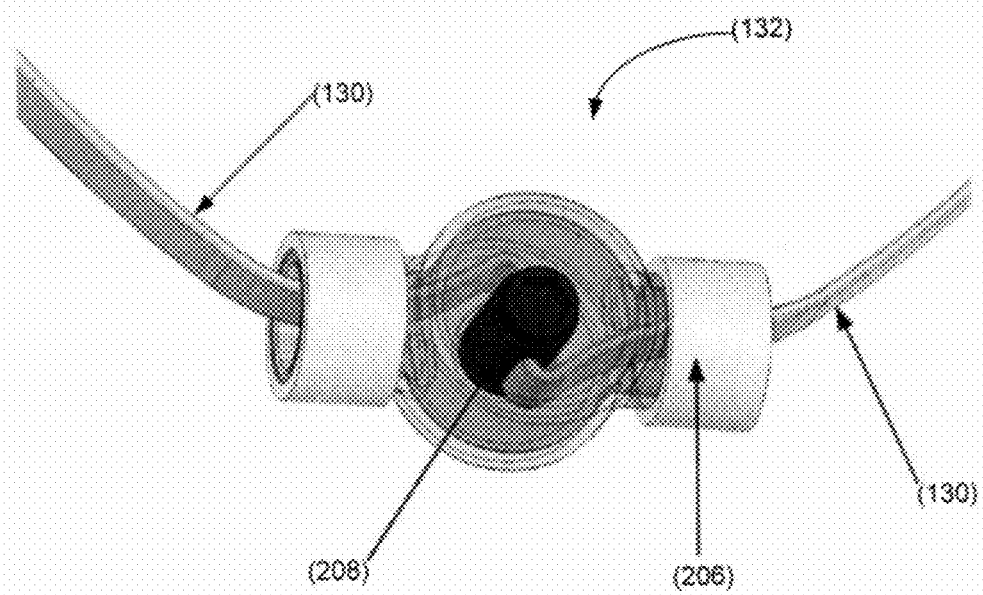

Another embodiment of the cinching mechanism 132 involves a ratchet-like mechanism. FIG. 6B depicts the ratchet-like structure, whereby the ring core 130 passes through two collars 206 and wraps around a spool 208. The interior of the spool 208 consists of a gearwheel with teeth and a pawl that engages the teeth (not shown) that adjusts the tension in the ring core 130. Like most ratchet-like structures, the spool 208 can be rotated to tighten the ring core 130 but prevents rotatable movement to loosen the ring core 130, once it is tightened. The device user rotates the spool 208 to tighten the ring core 130. The device user can manually release the ratchet mechanism by lifting the pawl so that it is clear of the teeth in order to rotate the spool 208 in either direction (for loosening or tightening the ring core 130). In another variation of this embodiment, a collar is securely attached to the spool and can be adjusted to cinch the ring core in place around the spool or allow it to freely turn in order to lock the ring core in place or adjust the circumference of the ring core.

Figure 6D:
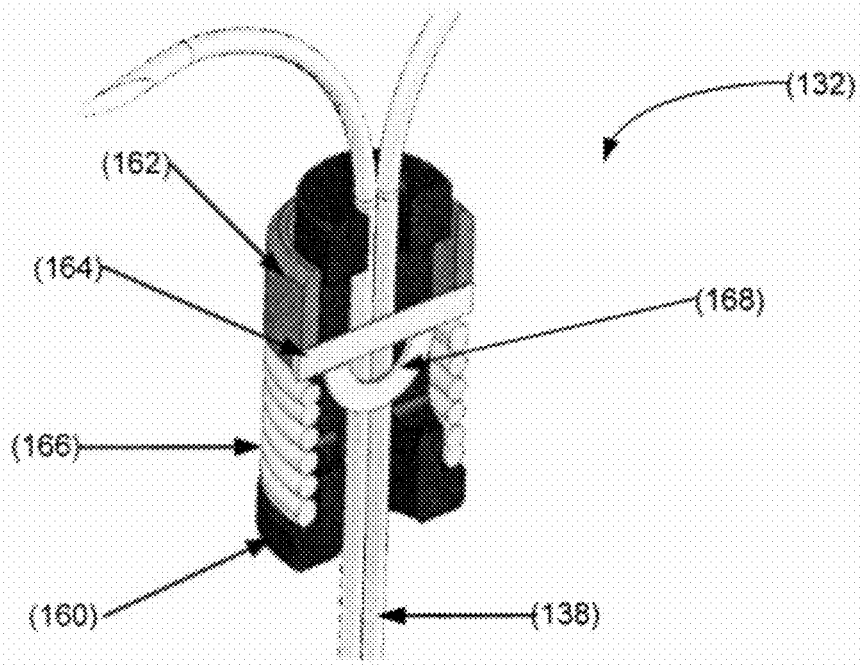

Another embodiment of the cinching mechanism 132 involves a wedge-pin cinching system (FIG. 6C-D). This embodiment features a spring-loaded pushrod 160 that resides inside a collar 162 with a cross-mounted pin 164. The cinching cords 138 pass through the interior of the spring-loaded pushrod 160. The spring 166 of the spring-loaded pushrod 160 pushes on the cross-mounted pin 164 so as to jam and lock the cinching cords 138 in place. A half-washer 168 is attached to the cross-mounted pin 164. The half-washer cord is attached to the half-washer 168. When the device user pulls on the half-washer cord, the half-washer 168 releases the cross-mounted pin 164, thereby releasing the jam on the cinching cords 138 and effectively, unlocking them. When the half-washer cord (not shown) is released by the device user, the cross-mounted pin 164 returns to its jammed position and the ring is locked at the prescribed dimension.

Another embodiment of the cinching mechanism 132 involves a simple cam system.

Figure 6E:
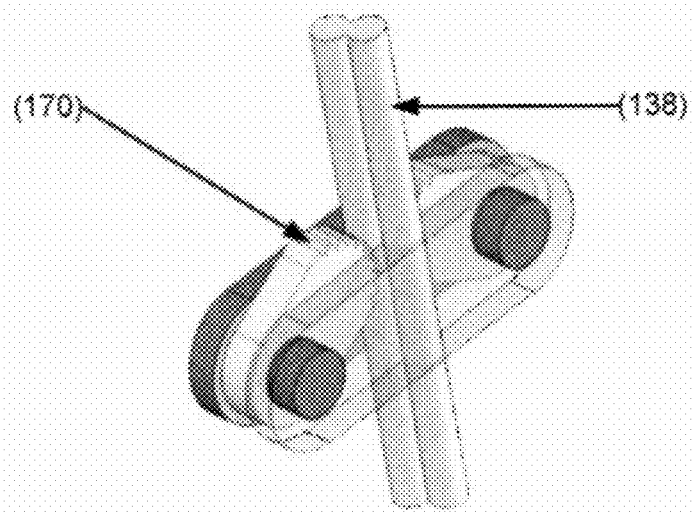

FIG. 6E depicts a cinching mechanism formed by two movable engagement structures in the form of opposing cams 170. In FIG. 2E the cams 170 are rotated to their open or unlocked position, whereby the cinching cords 138 move freely to adjust the circumference of the ring core (not shown). The cams 170 can also be rotated to their locked or engaging position wherein longitudinal movement of the cinching cords 138 is prevented and the ring core is locked into position.

FIGS. 7A-F illustrate another embodiment of the annular implant 120 in accordance with the present invention. In this embodiment, a reversible attachment apparatus 172 of the annular implant 120 is detailed. A series of retention barbs 182 is oriented to facilitate placement, retention, and removal of the reversible attachment apparatus 172, whereby the reversible attachment apparatus 172 may be used as an anchoring system for the annular implant or as an annular adjustment system. In either embodiment, the retention barbs 182 may be integrally formed with or fixedly attached to the interior of the annular implant 120. The retention barbs 182 can be composed of biocompatible material such as nitinol, stainless steel, cobalt-based alloy or combinations thereof.

Figure 7A:
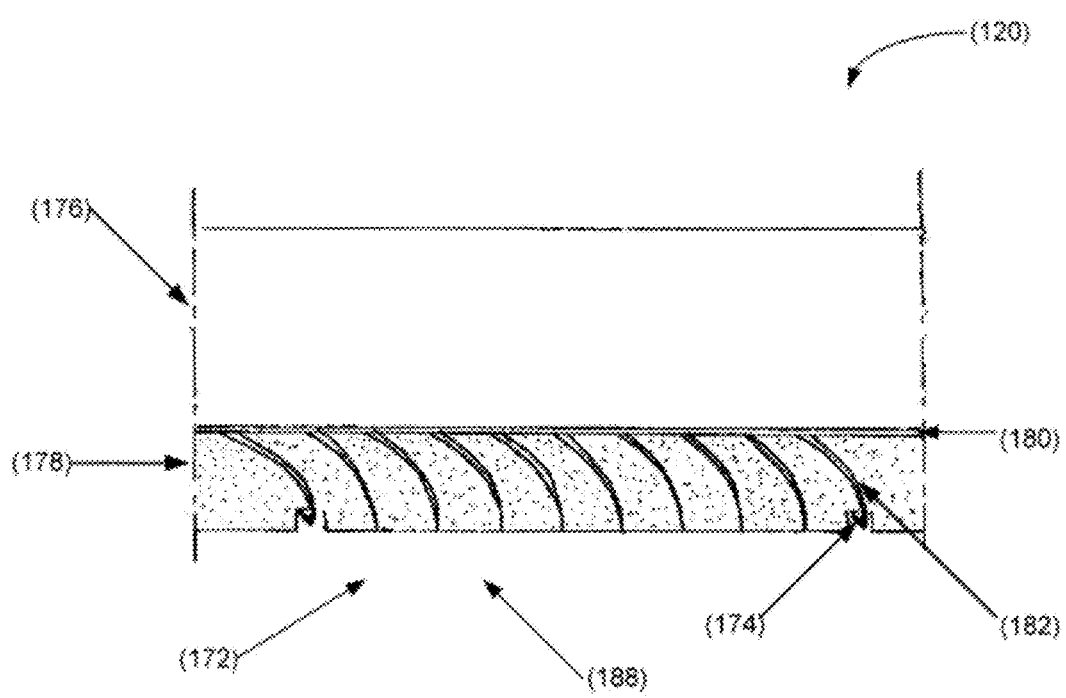

As further shown in FIG. 7A, the exemplary embodiment of the reversible attachment apparatus 172 of the annular implant 120 employs unidirectional retention barbs 182. The retention barbs 182 are oriented in a consistent, tangential position with respect to the annular implant 120. The retention barbs 182 may be further provided with a terminal hook 174 at the end, which allows for firm anchoring of the annular implant 120 into the surrounding valve annulus without permitting the annular implant 120 to rotate. The terminal hooks 174, like barbed fish hooks, ensure the seating of the annular implant 120 into the surrounding tissue.

The annular implant 120 contains an upper compartment 176 and a lower compartment 178, which houses the retention barbs 182 and terminal hooks 174. The compartments are divided by a movable retainer guide 180, which controls the action of the retention barbs 182 via a worm gear (described below). The upper compartment 176 may be composed of the ring core. The lower compartment 178 may be composed of foam or a foam-like material such as polyurethane foam, XPS foam, Styrofoam or some other manufactured foam encasing the retention barbs 182 until deployed. The exterior of the annular implant 120 (housing the upper and lower compartments) in such an embodiment may be fabricated of a biologically compatible material, such as Dacron, PTFE, malleable metals, other biologically compatible materials, or a combination of such biologically compatible materials in a molded, woven, or non-woven configuration.

FIG. 7B depicts one retention barb/terminal hook apparatus 182, 174 housed inside the lower compartment 178 of the annular implant 120. The retention barb housing 184 is a cleft on the inner surface of the lower compartment 178 of the annular implant 120 which prevents the retention barb 182 from engaging the valve annulus 188 prior to deployment. Additionally, the retention barb housing 184 serves as a guide for the terminal hook 174 upon deployment into the valve annulus 188. The terminal hook limiter 186 keeps the terminal hook 174 positioned for proper deployment.

FIGS. 7C and 7D illustrate an embodiment of the reversible attachment apparatus 172 of the annular implant 120 in which the lower compartment 178 includes retention barbs 182 and retention barb/terminal hook apparatuses 182, 174, which are movable between extended and retracted positions. In the retracted position shown in FIG. 7C, the retention barbs 182 and the retention barb/terminal hook apparatuses 182, 174 do not engage the valve annulus. When the movable retainer guide 180 is pulled in the direction of the arrow in FIG. 7C, the retention barbs 182 and retention barb/terminal hook apparatuses 182, 174 extend through the lower compartment 178 and into the valve annulus 188, as depicted in FIG. 7D. The terminal hooks 174 act like anchors to fix the annular implant 120 to the valve annulus 188.

FIGS. 7E-G illustrate the variable modes of the reversible attachment apparatus of the annular implant. FIG. 7E depicts the compressed mode, whereby the device is in position to be inserted into the canula trochar or catheter. FIG. 7F depicts post-insertion deployed mode, whereby the annular implant 120 rests passively on top of the valve annulus 188 with the lower compartment 178 expanded. FIG. 7G depicts the activated mode, whereby the annular implant 120 is attached to the valve annulus 188 via the retention barb/terminal hook apparatuses 182, 174.

The drive mechanism 192, depicted in FIGS. 7E-G, contains and supports a mechanical worm gear with an attached first gear head 210 which mates with a second gear head 212. The second geared head 212 is attached to an adjustment stem 214 which is machined to receive a screwdriver-like adjustment element. The various embodiments according to the present invention may require a number of forms of adjustment elements. In the present example, the adjustment element is provided as a finely coiled wire with a distal tip machined to be received by a receiving slot (not shown) in the adjustment stem 214. The relationship between the distal tip of the adjustment element and the adjustment stem 214 is mechanically similar to a screwdriver bit and screwhead, such that torsion imparted to the adjustment means by the device user will result in turning the adjustment stem 214 and a second geared head 212. This turning of the adjustment stem 214 and the second geared head 212 allows motion of the first geared head 210 and worm, which creates motion of the movable retainer guide 180 as the worm engages with a series of adjustment stops. The adjustment stops may be slots, holes, detents, dimples, ridges, raised elements, or other mechanical features.

FIGS. 8A-D depict the control interface 196, which acts as the main controller of the annular implant delivery device. The control interface 196 incorporates a plurality of attachment activator buttons 198, each of which drives a single attachment element (not shown) into the annular implant and valve annulus by remotely controlling the movement of the each gunbarrel pusher. Attachment of a two-button activation device 200 to an individual attachment activator button 198 allows the device user to control the delivery of the hollow insert (not shown) and the attachment element (not shown). When the device user pushes the hollow insert button 202 of the two-button activation device 200, the hollow insert (not shown) is driven through the annular implant and into the annular tissue. When the device user pushes the gunbarrel pusher button 204 of the two-button activation device 200, the gunbarrel pusher (not shown) is activated, thereby driving the attachment element (not shown) into the annular implant and valve annulus. If both the attachment activator button 198 and the gunbarrel pusher button 204 of the two-button activation device 200 are pushed simultaneously, the hollow insert (not shown) and the gunbarrel element (not shown) are driven into the annular implant and valve annulus.

In a preferred embodiment, deployment of the hollow insert and attachment element is as follows: first the user depresses the two-button activation device 200 that simultaneously advances the hollow insert and the gunbarrel pusher (not shown). The tip of the hollow insert penetrates into the annulus tissue. This penetration depth may be controlled by placing a mechanical stop in the pushbutton system to limit the depth of penetration of the hollow insert. Second, the user depresses a button to advance the gunbarrel pusher. As the gunbarrel pusher is advanced, it pushes the attachment element out of the distal tip of the hollow insert and into annular tissue. This penetration depth may also be controlled by a mechanical stop and is roughly equal to half of the length of the attachment element. Third, the user withdraws the hollow insert while holding the gunbarrel pusher in contact with the proximal end of the attachment element. This action strips the attachment element out of the hollow insert while keeping the attachment element at its intended penetrated depth of the annulus. Fourth, as the retreating hollow insert releases the proximal end of the attachment element, the attachment element springs to its curved shape, capturing the anchoring block and holding it against the annulus.

Once the annular implant is successfully attached to the valve annulus via any one of the aforementioned embodiments, the annular implant delivery device is removed from the patient's body and the Ramel or purse-string tourniquet is further tightened and tied off. The chest incision can then be closed. In various embodiments, the annular implant delivery device may be configured to allow re-introduction for adjustment of the annular implant. Furthermore, alternate methods for use of an adjustable implant may provide for periodic, post-implantation adjustment of the size of the implant to fit the valve annulus as needed to accommodate growth of the site in a juvenile patient or other physiologic changes and needs of the patient.

The present invention and the methods for its use anticipate many alternate embodiments in other potential applications in the broad fields of medicine and surgery. Among the other potential applications anticipated according to the present invention are adjustable implants for use in the treatment of morbid obesity, urinary incontinence, anastomotic strictures, arterial stenosis, cervical incompetence, ductal strictures, and anal incontinence. The preceding discussions are intended to be exemplary embodiments according to the present invention and should not be construed to limit the present invention and the methods for its use in any way. Other features and embodiments of the present invention will be apparent to those in the art in view of the present disclosure.

What is claimed is:

1. A delivery device for an annular implant comprising:
   a balloon expansion mechanism, wherein the balloon expansion mechanism comprises a hollow catheter attached to an inflation tube whereby a gas or liquid is fed through said inflation tube and a non-occluding balloon collar attached to the inflation tube to provide for expansion of the balloon collar, wherein the balloon collar is supported by a plurality of trusses radially extending from the hollow catheter;
   an annular implant having an adjustable dimension removably mounted around the non-occluding balloon collar;
   a plurality of gunbarrel elements, wherein each gunbarrel element contains a hollow insert and a gunbarrel pusher and wherein the gunbarrel pusher drives an attachment element into the annular implant and annular tissue;
   a plurality of anchoring blocks attached to the annular implant, wherein each gunbarrel element is anchored into a corresponding anchoring block;
   a plurality of contiguous coiled spacers coiled along the annular implant, wherein each coiled spacer keeps each pair of anchoring blocks equidistant as the annular implant diameter is manipulated;
   a trocar releasably housing the gunbarrel elements; and
   a proximal control interface having control mechanisms for inflation of the balloon collar and deployment of the attachment elements.

2. The delivery device of claim 1, wherein the balloon collar is either cylindrical or spherical in shape.

3. The delivery device of claim 1, wherein the balloon collar is any size or shape suitable for deployment in a lumen.

4. The delivery device of claim 1, wherein the balloon collar is made of a flexible biocompatible material.

5. The delivery device of claim 1, wherein a check valve is incorporated into the balloon expansion mechanism.

6. The delivery device of claim 1:
   wherein the annular implant comprises a flexible ring core and wherein the flexible ring core is adjustable through two cinching cords;
   and further comprising a cinching mechanism attached to the flexible ring core, wherein said cinching mechanism reshapes the annular implant to conform to the size and shape of an annulus via the cinching cords.

7. The delivery device of claim 6, wherein the cinching mechanism comprises a wedge-pin mechanism.

8. The delivery device of claim 1, wherein the trocar houses an alignment disc, wherein the alignment disc provides separation to the gunbarrel elements during device introduction.

9. The delivery device of claim 1, wherein said control interface comprises:
   a plurality of attachment activator buttons, wherein each attachment activator button has the capacity to drive a single attachment element and hollow insert into the annular implant and valve annulus; and
   a two-button activation device wherein said two-button activation device attaches to each attachment activator button individually, which allows the device user to control delivery of the hollow insert and the attachment element into the annular implant and valve annulus.

10. A delivery system for an annular implant comprising:
    a balloon expansion mechanism comprising an inflatable tubular balloon collar having a cylindrical shape defining an annulus, a hollow catheter extending within the annulus, a plurality of spaced apart trusses arranged within the annulus for supporting the balloon collar about the catheter, and an inflation tube in fluid communication with the balloon collar for expansion of the balloon collar by a fluid supplied therefrom;
    an annular implant having an adjustable dimension removably coupled to the balloon expansion mechanism;
    a plurality of gunbarrel elements, wherein each gunbarrel element contains a hollow insert and a gunbarrel pusher and wherein the gunbarrel pusher drives an attachment element into the annular implant and annular tissue;
    a plurality of anchoring blocks attached to the annular implant, wherein each gunbarrel element is anchored into a corresponding anchoring block;
    a plurality of contiguous coiled spacers coiled along the annular implant, wherein each coiled spacer keeps each pair of anchoring blocks equidistant as the annular implant diameter is manipulated;
    a trocar releasably housing the gunbarrel elements; and
    a proximal control interface having control mechanisms for inflation of the balloon collar and deployment of the attachment elements.

* * * * *